(12) United States Patent
Knappe et al.

(10) Patent No.: US 9,044,411 B2
(45) Date of Patent: Jun. 2, 2015

(54) AGENT FOR KERATINOUS FIBERS, COMPRISING AT LEAST ONE ACRYLATE/GLYCERYL ACRYLATE COPOLYMER, AT LEAST ONE FILM-FORMING AND/OR SOLIDIFYING POLYMER AND AT LEAST ONE ESTER OIL

(71) Applicant: Henkel AG & Co. KGaA, Duesseldorf (DE)

(72) Inventors: Thorsten Knappe, Schenefeld (DE); Helga van Flodrop, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/042,687

(22) Filed: Sep. 30, 2013

(65) Prior Publication Data
US 2014/0050686 A1   Feb. 20, 2014

Related U.S. Application Data

(60) Division of application No. 13/354,390, filed on Jan. 20, 2012, now abandoned, which is a continuation of application No. PCT/EP2010/060297, filed on Jul. 16, 2010.

(30) Foreign Application Priority Data

Jul. 22, 2009 (DE) .................. 10 2009 027 925

(51) Int. Cl.
*A61Q 5/06* (2006.01)
*A61K 8/81* (2006.01)
*A61K 8/37* (2006.01)

(52) U.S. Cl.
CPC .......... *A61K 8/8152* (2013.01); *A61K 8/37* (2013.01); *A61K 8/8111* (2013.01); *A61K 8/8164* (2013.01); *A61K 8/8176* (2013.01); *A61K 8/8182* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 4,402,977 | A | 9/1983 | Grollier et al. |
| 4,994,265 | A | 2/1991 | White |
| 6,407,056 | B1 | 6/2002 | Seiberg et al. |
| 6,569,413 | B1 | 5/2003 | Hessefort et al. |
| 6,620,409 | B2 | 9/2003 | Bossmann et al. |
| 7,332,466 | B2 | 2/2008 | Schmid et al. |
| 7,820,152 | B2 | 10/2010 | McLaughlin et al. |

FOREIGN PATENT DOCUMENTS

| | | |
|---|---|---|
| DE | 19738866 A1 | 3/1999 |
| WO | 94/08555 A1 | 4/1994 |
| WO | 99/22697 A1 | 5/1999 |
| WO | 2005/016291 A1 | 2/2005 |
| WO | 2010/059458 A2 | 5/2010 |

OTHER PUBLICATIONS

PCT International Search Report (PCT/EP2010/060297) dated Jun. 24, 2011.
"A New High-Spreading Ester Emollient for Hair Care Applications" Research Disclosure, Mason Publications, Dec. 1, 2007, p. 1182.
"A New High-Spreading Ester Emollient for the Hair Care Market" Research Disclosure, Mason Publications, Oct. 1, 2006, p. 1302.

*Primary Examiner* — Jyothsna Venkat
(74) *Attorney, Agent, or Firm* — P. Scott Smith

(57) ABSTRACT

The present invention is an agent for treating keratinous fibers, particularly human hair, comprising: (a) at least one glyceryl acrylates/acrylates copolymer; (b) at least one film-forming and/or setting polymer; and (c) at least one ester oil. The agent may additionally comprise a polyol such as glycerin. The agent is best suited for temporarily deforming hairs into a desired shape or style and for the general caring of hair.

16 Claims, No Drawings

AGENT FOR KERATINOUS FIBERS, COMPRISING AT LEAST ONE ACRYLATE/GLYCERYL ACRYLATE COPOLYMER, AT LEAST ONE FILM-FORMING AND/OR SOLIDIFYING POLYMER AND AT LEAST ONE ESTER OIL

CROSS-REFERENCE TO RELATED APPLICATION

This application is a divisional of U.S. application Ser. No. 13/354,390, filed on Jan. 20, 2012, which is a continuation of PCT Application Serial No. PCT/EP2010/060297, filed on Jul. 16, 2010, which claims priority under 35 U.S.C. §119 to 10 2009 027 925.3 (DE) filed on Jul. 22, 2009. The disclosures PCT/EP2010/060297 and DE 10 2009 027 925.3 are hereby incorporated by reference in their entirety.

FIELD OF THE INVENTION

The present invention relates to agents for the treatment of hair, comprising a combination of at least one acrylate-glyceryl acrylate copolymer, at least one film-forming and/or setting polymer, and at least one ester oil. The present invention also relates to a method for the cosmetic treatment of keratin-containing fibers.

BACKGROUND OF THE INVENTION

Keratin-containing fibers are in principle understood to include all animal hair, e.g. wool, horsehair, angora hair, furs, feathers and products or fabrics produced from them. However, the keratinic fibers preferably concern human hair.

Today, a suitably looking hairstyle is generally regarded as an essential part of a well groomed appearance. Based on current fashion trends, time and again hairstyles are considered chic, which, for many types of hair, can only be formed or sustained over a longer period of up to several days by the use of certain setting materials. Thus, hair treatment agents that provide a permanent or temporary hairstyling play an important role. Temporary styling intended to provide a good hold, without compromising the healthy appearance of the hair, such as, for example their gloss, can be obtained for example by the use of hairsprays, hair waxes, hair gels, hair foams, setting lotions etc.

Suitable compositions for temporary hairstyling usually comprise synthetic polymers, so called setting polymers, as the styling component. Preparations comprising a dissolved or dispersed polymer can be applied on the hair by means of propellants or by a pumping mechanism. Hair gels and hair waxes in particular are however not generally applied directly on the hair, but rather dispersed with a comb or by hand.

An important property of an agent for the temporary styling of keratinic fibers, in the following also called styling agents, consists in giving the treated fibers the strongest possible hold in the created shape. If the keratinic fibers concern human hair, then one also speaks of a strong hairstyle hold or a high degree of hold of the styling agent. The styling hold is determined essentially by the type and quantity of the synthetic polymer used, but there may also be an influence from the other components of the styling agent. Ideally these polymers form a polymer film when applied to hair, imparting on the one hand a strong hold to the hairstyle but on the other hand also being sufficiently flexible not to break under stress. If the polymer film is too brittle, so-called film plaques develop, i.e. residues that are shed with movement of the hair and give the impression that the user of the respective styling agent has dandruff.

In addition to a high degree of hold, styling agents must fulfill a whole series of additional requirements. These requirements can be broadly subdivided into properties on the hair, properties of the formulation in question, e.g. properties of the foam, the gel or the sprayed aerosol, and properties that concern the handling of the styling agent, wherein particular importance is attached to the properties on the hair. In particular, moisture resistance, low stickiness and a balanced conditioning effect should be mentioned.

To develop styling agents that in combination have all the desired properties still presents problems. This particularly applies to the combination of esthetic factors on the one hand and to the strong and flexible hold on the other hand. In order to impart a strong hold, the setting polymer has to adhere well to the keratin-containing fibers and form a sufficiently hard film. Nevertheless, the resulting polymer film should not lend the tactility of a board to the collective fibers, but rather impart a degree of flexibility to the fibers, without losing the marked styling of the collective fibers, i.e. a hair style.

Accordingly, the object of the present invention was to provide an agent for the temporary styling of keratinic fibers, which is characterized by a very high degree of hold and excellent care properties of the keratin-containing fibers.

SUMMARY OF THE INVENTION

It has now been surprisingly found that a very high degree of hold and excellent care properties of keratin-containing fibers can be achieved by the inventive combination of at least one acrylate-glyceryl acrylate copolymer, at least one film-forming and/or setting polymer and at least one ester oil. Agents according to the invention can be very well dispersed on the hair, lend a perfect hold to the hair style and well cared-for keratinic fibers at the same time.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

With that said, one embodiment of the present invention comprises agents for treating keratin-containing fibers, especially human hair, comprising in a cosmetically acceptable carrier:

(a) at least one copolymer containing at least one structural unit of Formula (I) and at least one structural unit of Formula (II):

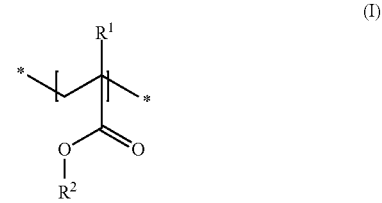

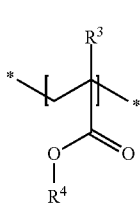

wherein $R^1$ and $R^3$ independently of one another stand for a hydrogen atom or a methyl group;
$R^2$ stands for a dihydroxypropyl group (preferably 2,3-dihydroxypropyl) that can be substituted with a glyceryl group or an oligoglyceryl group of 2 to 10 glyceryl units; and
$R^4$ stands for a hydrogen atom or a ($C_1$ to $C_4$) alkyl group;
(b) at least one film-forming and/or setting polymer; and
(c) at least one ester oil.

In the above Formulas, and all Formulas below, the symbol * signifies a chemical bond that stands for a free valence of the corresponding structural fragment.

Preferred $R^4$ groups above are chosen from the group consisting of methyl, ethyl, propyl, isopropyl, butyl, sec-butyl, isobutyl, and tert-butyl.

Preferred dihydroxypropyl groups above are chosen from the group consisting or 1,3-dihydroxyprop-2-yl and 2,3-dihydroxypropyl.

The agents according to the invention preferably comprise the copolymers of the components (a) in an amount of 0.001 wt % to 1.0 wt %, particularly preferably 0.005 wt % to 0.5 wt %, and quite particularly preferably 0.005 wt % to 0.1 wt %, each based on the weight of the agent.

Preferred suitable copolymers of the components (a) are those that comprise at least one structural unit of Formula (II), in which $R^1$ stands for a hydrogen atom.

Particularly preferred copolymers (a) are those that comprise at least one structural unit of Formula (I-1) as Formula (I):

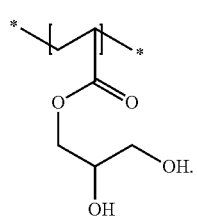

Furthermore, the inventive agent preferably comprises as the component (a) at least one copolymer having at least one structural unit of the Formula (II), in which $R^4$ is hydrogen. In this regard, it is again preferred that $R^3$ in this structural unit is also a hydrogen atom.

Quite particularly preferred inventive agents comprise as the component (a) at least one copolymer that is a copolymer of glyceryl acrylate and acrylic acid. Among these, such copolymers with the INCI name Gycerylacrylate/Acrylates are preferred.

The agent according to the invention imperatively comprises at least one film-forming cationic and/or setting polymer in addition to the copolymer (a) and the ester oil (c). These film forming polymers are different from the copolymers (a).

The preferred properties of the film-forming polymers include the film formation. Film-forming polymers are understood to mean those polymers that on drying leave a continuous film on the skin, the hair or the nails. These types of film-former can be used in the widest variety of cosmetic products such as, for example make up masks, make up, hair sets, hair sprays, hair gels, hair waxes, hair conditioners, shampoos or nail varnishes. Those polymers are particularly preferred, which are sufficiently soluble in alcohol or water/alcohol mixtures, such that they are present in completely dissolved form in the agent according to the invention. The film-forming polymers can be of synthetic or of natural origin.

According to the invention, film-forming polymers are further understood to mean those polymers that, when used in concentrations of 0.01 to 20 wt % in aqueous, alcoholic or aqueous alcoholic solution, are able to precipitate out a transparent polymer film on the hair.

Setting polymers contribute to the hold and/or to the creation of the hair volume and the hair body of the whole hairstyle. These polymers are also film-forming polymers at the same time and therefore in general are typical substances for styling hair treatment agents such as hair sets, hair foams, hair waxes, and hair sprays. The film formation can be in completely selected areas and bond only some fibers together.

The so-called curl-retention test is frequently used as a test method for the setting action.

As polymers are often multifunctional, i.e. show a plurality of desired end-use effects, a large number of polymers are to be found in many of the groups subdivided according to the mode of action, therefore also in the CTFA Handbook.

The agent according to the invention preferably comprises the film-forming and/or setting polymers in an amount of 0.01 wt % to 20.0 wt %, particularly preferably 0.5 wt % to 15 wt %, and quite particularly preferably 2.0 wt % to 10.0 wt %, each based on the weight of the agent. These quantities also apply for all subsequent preferred types of film-forming and/or setting polymers that can be used in the inventive agents. In the case that subsequently different preferred quantities are specified, then the latter are to be again taken as the preferred quantities.

The inventive powdered composition preferably includes a film-forming and/or setting polymer chosen from the group consisting of at least one cationic film-forming and/or cationic setting polymer, at least one non-ionic film-forming and/or non-ionic setting polymer, at least one anionic film-forming and/or anionic setting polymer, at least one amphoteric film-forming and/or amphoteric setting polymer, and mixtures thereof.

The inventive powdered composition more preferably includes a film-forming and/or setting polymer chosen from the group consisting of at least one cationic film-forming and/or cationic setting polymer, at least one non-ionic film-forming and/or non-ionic setting polymer, and mixtures thereof.

In the context of a further embodiment, the inventive powdered compositions comprise as the film-forming and/or setting polymer a cationic film-forming and/or cationic setting polymer.

The cationic film-forming and/or cationic setting polymers preferably possess at least one structural unit that comprises at least one permanently cationic nitrogen atom. A permanently cationic nitrogen atom is understood to mean those nitrogen atoms that carry a positive charge and thereby form a quaternary ammonium compound. Quaternary ammonium compounds are mostly produced by reacting tertiary amines with alkylating agents, such as, for example, methyl chloride, benzyl chloride, dimethyl sulfate, dodecyl bromide, but also ethylene oxide. Depending on the tertiary amine, the following groups are particularly well known: alkylammonium compounds, alkenylammonium compounds, imidazolinium compounds and pyridinium compounds.

In the context of the invention, preferred powdered compositions comprise the film-forming cationic and/or setting cationic polymers in an amount of 0.1 wt % to 20.0 wt %, particularly preferably 0.2 wt % to 10.0 wt %, and quite particularly preferably 0.5 wt % to 5.0 wt %, each based on the weight of the composition.

According to the invention, the cationic film-forming and/or cationic setting polymers can be selected from cationic, quaternized cellulose derivatives.

In general, those cationic, quaternized celluloses that carry more than one permanent cationic charge in a side chain have proven to be advantageous in the context of the invention.

Among the preferred cationic cellulose derivatives are those produced from the reaction of hydroxyethyl cellulose with a dimethyldiallylammonium reactant (especially dimethyldiallylammonium chloride) optionally in the presence of further reactants. Among these cationic celluloses, once again those cationic celluloses with the INCI name Polyquaternium-4 are particularly suitable, which, for example, are marketed by the National Starch company under the trade names Celquat® H 100, Celquat® L 200.

In addition, such cationic film-forming and/or cationic setting polymers that contain at least one structural unit of Formula (M-I) and at least one structural unit of Formula (M-VI) and optionally at least one structural unit of Formula (M-V) are suitable;

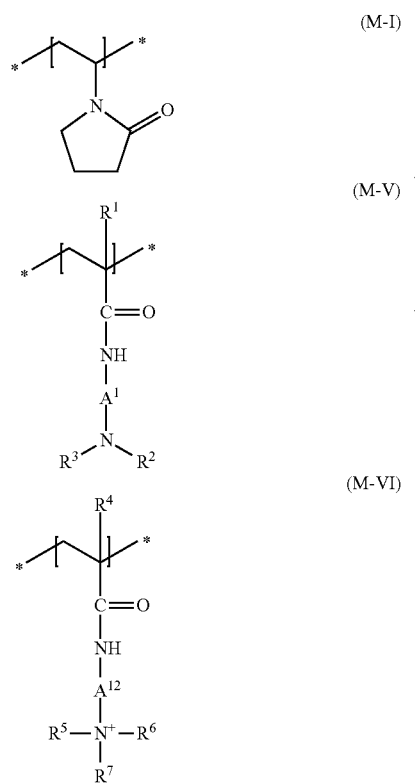

wherein;
R$^1$ and R$^4$ independently of one another stand for a hydrogen atom or a methyl group;

A$^1$ and A$^2$ stand independently of one another for an ethane-1,2-diyl, propane-1,3-diyl or butane-1,4-diyl group;
R$^2$, R$^3$, R$^5$ and R$^6$ stand independently of one another for a (C$_1$ to C$_4$) alkyl group; and
R$^7$ stands for a (C$_8$ to C$_{30}$) alkyl group.

To compensate for the positive charge of the monomer (M-VI), all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate, p-toluene sulfonate, or triflate.

Exemplary suitable compounds are commercially available as: copolymers of dimethylaminoethyl methacrylate, quaternized with diethyl sulfate, with vinyl pyrrolidone having the INCI name Polyquaternium-11 under the trade names Gafquat® 440, Gafquat® 734, Gafquat® 755 (each from ISP) and Luviquat PQ 11 PN (BASF SE); copolymers of methacryloylaminopropyllauryldimethylammonium chloride with vinyl pyrrolidone and dimethylaminopropylmethacrylamide with the INCI name Polyquaternium-55 under the trade names, Styleze® W-10, Styleze® W-20 (ISP); and, copolymers of N-vinyl pyrrolidone, N-vinyl caprolactam, N-(3-dimethylaminopropyl)methacrylamide and 3-(methacryloylamino)propyl-lauryl-dimethylammonium chloride (INCI name: Polyquaternium-69) under the trade name Aquastyle® 300 (28-32 wt % active substance in water/ethanol) (ISP).

In the context of the invention, in addition, those cationic film-forming and/or cationic setting copolymers that comprise at least one structural element of the Formula (M1) serve as the particularly preferred usable film-forming and/or setting polymers selected from cationic polymers that comprise at least one structural unit that possess a quaternary positively charged nitrogen atom:

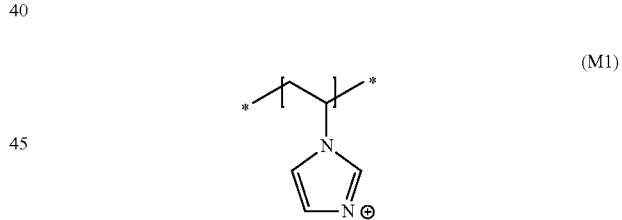

wherein R" stands for a (C$_1$ to C$_4$) alkyl group, especially a methyl group, and additionally possesses at least one other cationic and/or non-ionic structural element.

To compensate for the positive polymer charge of the component, all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate, p-toluene sulfonate, or triflate.

It is again inventively preferred if the powdered composition according to the invention comprises as the cationic film-forming and/or cationic setting polymer of this embodiment at least one copolymer (b1) that in addition to a structural element of Formula (M1), further contains a structural element of Formula (M-I):

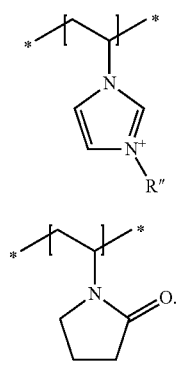

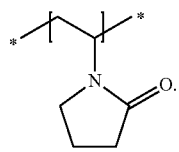

wherein R″ stands for a ($C_1$ to $C_4$) alkyl group, particularly a methyl group.

To compensate for the positive polymer charge of the copolymer (b1), all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate, p-toluene sulfonate, or triflate.

Quite particularly preferred cationic film-forming and/or cationic setting polymers as the copolymers (b1) comprise 10 to 30 mol %, preferably 15 to 25 mol % and particularly 20 mol % of structural units in accordance with Formula (M1) and 70 to 90 mol %, preferably 75 to 85 mol % and particularly 80 mol % of structural units in accordance with Formula (M-I).

In this regard it is particularly preferred when the copolymers (b1) comprise, in addition to polymer units that result from the incorporation of the cited structural units in accordance with Formula (M1) and (M-I) into the copolymer, maximum 5 wt %, preferably maximum 1 wt % of polymer units that trace back to the incorporation of other monomers. The copolymers (b1) are preferably exclusively constituted from structural units of Formula (M1) with R″=methyl and (M-I), and can be described by the general Formula (Poly1):

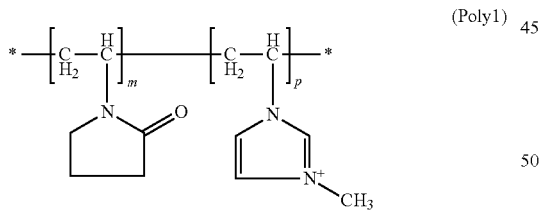

wherein each of the indices m, and p vary according to the molecular mass of the polymer and are not intended to mean to portray block copolymers. In fact, structural units of Formula (M1) and Formula (M-I) can be statistically distributed in the molecule.

If a chloride ion is used to compensate the positive charge of the polymer of Formula (Poly1), then these N-methyl vinyl imidazole/vinyl pyrrolidone copolymers are named according to INCI nomenclature as Polyquaternium-16 and are available from for example BASF under the trade names Luviquat® Style, Luviquat® FC 370, Luviquat® FC 550, Luviquat® FC 905 and Luviquat® HM 552.

If a methosulfate ion is used to compensate the positive charge of the polymer of Formula (Poly1), then these N-methyl vinyl imidazole/vinyl pyrrolidone copolymers are named according to INCI nomenclature as Polyquaternium-44 and are available from for example BASF under the trade name Luviquat® UltraCare.

Particularly preferred inventive powdered compositions comprise a copolymer (b1), especially of Formula (Poly1), which has molecular masses within a defined range. Here, inventive agents are preferred, in which the molecular mass of the copolymer (b1) is from 50 to 400 kDa, preferably from 100 to 300 kDa, more preferably from 150 to 250 kDa and particularly from 190 to 210 kDa.

In addition to the copolymer(s) (c1) or instead of it or them, the inventive powdered compositions can also comprise copolymers (b2) that starting from the copolymer (c1) possess as the additional structural units structural units of the Formula (M-II):

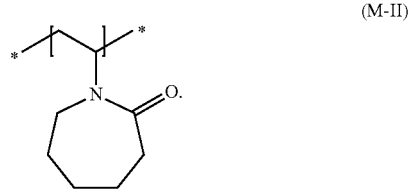

Further particularly preferred powdered compositions according to the invention are accordingly those that comprise as the cationic film-forming and/or cationic setting polymer at least one copolymer (b2) that comprises at least one structural unit according to Formula (M1-a) and at least one structural unit according to Formula (M-I) and at least one structural unit according to Formula (M-II):

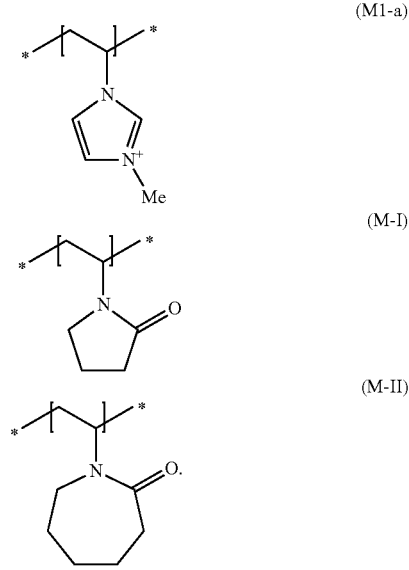

Also in this regard it is particularly preferred when the copolymers (b2) comprise, in addition to polymer units that result from the incorporation of the cited structural units in accordance with Formula (M1-a), (M-I) and (M-II) into the copolymer, maximum 5 wt %, preferably maximum 1 wt % of polymer units that trace back to the incorporation of other monomers. The copolymers (b2) are preferably exclusively constituted from structural units of Formula (M1-a), (M-I) and (M-II) and can be described by the general Formula (Poly2):

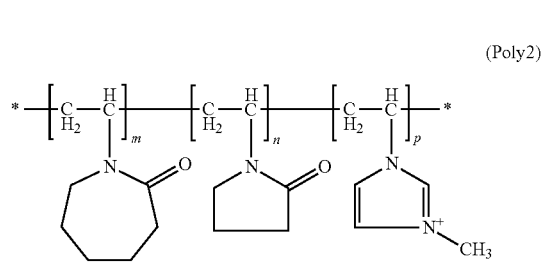
(Poly2)

wherein each of the indices m, n and p vary according to the molecular mass of the polymer and are not intended to mean to portray block copolymers. In fact, structural units of the cited Formulas can be statistically distributed in the molecule.

To compensate for the positive polymer charge of the component (b2), all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate, p-toluene sulfonate, or triflate.

If a methosulfate ion is used to compensate the positive charge of the polymer of Formula (Poly2), then these N-methyl vinyl imidazole/vinyl pyrrolidone/vinyl caprolactam copolymers are named according to INCI nomenclature as Polyquaternium-46 and are available from for example BASF under the trade name Luviquat® Hold.

Quite particularly preferred copolymers (b2) comprise 1 to 20 mol %, preferably 5 to 15 mol % and particularly 10 mol % of structural units in accordance with Formula (M1-a) and 30 to 50 mol %, preferably 35 to 45 mol % and particularly 40 mol % of structural units in accordance with Formula (I) and 40 to 60 mol %, preferably 45 to 55 mol % and particularly 60 mol % of structural units in accordance with Formula (M-II).

Particularly preferred inventive powdered compositions comprise a copolymer (b2) that has molecular masses within a defined range. Here, inventive agents are preferred, in which the molecular mass of the copolymer (b2) is from 100 to 1000 kDa, preferably from 250 to 900 kDa, more preferably from 500 to 850 kDa and particularly from 650 to 710 kDa.

In addition to the copolymer(s) (b1) and/or (b2) or in its or their place the powdered compositions according to the invention can also comprise copolymers (b3) as the film-forming cationic and/or setting cationic polymer which possess as the structural units structural units of the Formulas (M1-a) and (I), as well as additional structural units from the group of the vinyl imidazole units and further structural units from the group of the acrylamide and/or methacrylamide units.

Further particularly preferred powdered compositions according to the invention are accordingly those that comprise as the cationic film-forming and/or cationic setting polymer at least one copolymer (b3) that comprises at least one structural unit according to Formula (M1-a) and at least one structural unit according to Formula (M-I) and at least one structural unit according to Formula (M-VII) and at least one structural unit according to Formula (M-VIII):

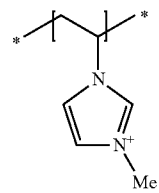
(M1-a)

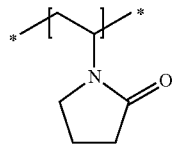
(M-I)

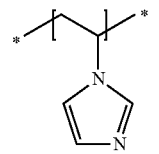
(M-VII)

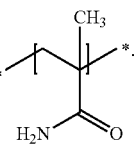
(M-VIII)

Also in this regard it is particularly preferred when the copolymers (b3) comprise, in addition to polymer units that result from the incorporation of the cited structural units in accordance with Formula (M1-a), (M-I), (M-VII) and (M-VIII) into the copolymer, maximum 5 wt %, preferably maximum 1 wt % of polymer units that trace back to the incorporation of other monomers. The copolymers (b3) are preferably exclusively constituted from structural units of Formula (M1-a), (M-I), (M-VII) and (M-VIII) and can be described by the general Formula (Poly3):

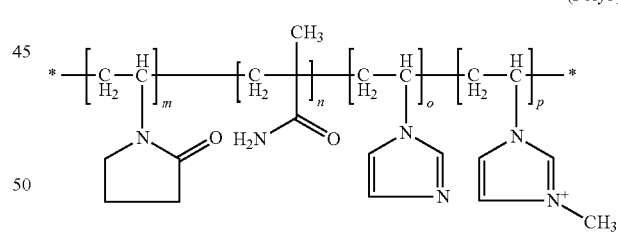
(Poly3)

wherein each of the indices m, n, o and p vary according to the molecular mass of the polymer and are not intended to mean to portray block copolymers. In fact, structural units of Formula (M1-a), (M-I), (M-VII) and (M-VIII) can be statistically distributed in the molecule.

To compensate for the positive polymer charge of the component (b2), all possible physiologically acceptable anions may be used, such as for example chloride, bromide, hydrogen sulfate, methyl sulfate, ethyl sulfate, tetrafluoroborate, phosphate, hydrogen phosphate, dihydrogen phosphate, p-toluene sulfonate, or triflate.

If a methosulfate ion is used to compensate the positive charge of the polymer of Formula (Poly3), then these N-methyl vinyl imidazole/vinyl pyrrolidone/vinyl imidazole/methacrylamide copolymers are named according to INCI nomenclature as Polyquaternium-68 and are available from for example BASF under the trade name Luviquat® Supreme.

Quite particularly preferred copolymers (b3) comprise 1 to 12 mol %, preferably 3 to 9 mol % and particularly 6 mol % of structural units in accordance with Formula (M1-a) and 45 to 65 mol %, preferably 50 to 60 mol % and particularly 55 mol % of structural units in accordance with Formula (M-I) and 1 to 20 mol %, preferably 5 to 15 mol % and particularly 10 mol % of structural units in accordance with Formula (M-VII) and 20 to 40 mol %, preferably 25 to 35 mol % and particularly 29 mol % of structural units in accordance with Formula (M-VIII).

Particularly preferred inventive agents comprise a copolymer (b3) that has molecular masses within a defined range. Here, inventive agents are preferred, in which the molecular mass of the copolymer (b3) is from 100 to 500 kDa, preferably from 150 to 400 kDa, more preferably from 250 to 350 kDa and particularly from 290 to 310 kDa.

Preferred additional film-forming cationic and/or setting polymers, selected from the cationic polymers with at least one structural element of the above Formula (M1), include (a) vinyl pyrrolidone/1-vinyl-3-methyl-1H-imidazolium chloride copolymers (such as for example that with the INCI name Polyquaternium-16, sold under the trade names Luviquat® Style, Luviquat® FC 370, Luviquat® FC 550, Luviquat® FC 905 and Luviquat® HM 552 (BASF SE)); (b) vinyl pyrrolidone/1-vinyl-3-methyl-1H-imidazolium methyl sulfate copolymers (such as for example that with the INCI name Polyquaternium-44 sold under the trade name Luviquat® Care (BASF SE)); (c) vinyl pyrrolidone/vinyl caprolactam/1-vinyl-3-methyl-1H-imidazolium terpolymer (such as for example that with the INCI name Polyquaternium-46 sold under the trade names Luviquat® Care or Luviquat® Hold (BASF SE)); (d) pyrrolidone/methacrylamide/vinyl imidazole/1-vinyl-3-methyl-1H-imidazolium methyl sulfate copolymer (such as for example that with the INCI name Polyquaternium-68 sold under the trade name Luviquat® Supreme (BASF SE)); and (e) mixtures of these polymers.

In the context of a preferred embodiment, the inventive powdered compositions comprise as the film-forming and/or setting polymer at least one film-forming non-ionic and/or setting non-ionic polymer.

According to the invention, a non-ionic polymer is understood to mean a polymer that in a protic solvent under standard conditions carries essentially no structural units containing cationic or anionic groups that have to be compensated by counter ions in order to maintain electroneutrality. Cationic groups include for example quaternized ammonium groups but no protonated amines. Anionic groups include for example carboxylic acid and sulfonic acid groups.

The agent according to the invention preferably comprises the non-ionic, film-forming and/or non-ionic, setting polymers in an amount of 0.1 wt % to 20.0 wt %, particularly preferably 0.2 wt % to 15.0 wt %, quite particularly preferably 0.5 wt % to 5.0 wt %, each based on the weight of the powdered composition according to the invention.

The film-forming non-ionic and/or setting non-ionic polymers are again preferably selected from at least one polymer of the group consisting of homopolymers and non-ionic copolymers of N-vinyl pyrrolidone, nonionic copolymers of isobutene, nonionic copolymers of maleic anhydride, and mixtures thereof.

In this regard, a combination of film-forming non-ionic and/or setting non-ionic polymers is preferred, containing at least one non-ionic copolymer of maleic anhydride and at least one polymer from the group consisting of homopolymers and non-ionic copolymers of N-vinyl pyrrolidone.

Suitable polyvinyl pyrrolidones are for example commercial products such as Luviskol® K 90 or Luviskol® K 85 from BASF SE.

Suitable polyvinyl alcohols are marketed for example under the trade names Elvanol® by Du Pont or Vinol® 523/540 by Air Products.

A suitable polyvinyl acetate is marketed for example as an emulsion under the trade name Vinac® by Air Products.

Preferably, the agents include a film-forming non-ionic and/or setting non-ionic polymer selected from the group consisting of copolymers of maleic anhydride and methyl vinyl ether, polyvinyl pyrrolidone, copolymers of N-vinyl pyrrolidone and vinyl esters of carboxylic acids containing 2 to 8 carbon atoms, especially from N-vinyl pyrrolidone and vinyl acetate, copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof.

In this regard it is again preferred when the molar ratio of the comprised structural units of the monomer N-vinyl pyrrolidone to the comprised structural units of the monomer vinyl acetate of the polymer is in the range of 20 to 80 to 80 to 20, in particular 30 to 70 to 60 to 40.

Suitable copolymers of vinyl pyrrolidone and vinyl acetate are available for example under the trade names Luviskol® VA 37, Luviskol® VA 55, Luviskol® VA 64 and Luviskol® VA 73 from BASF SE.

Further preferred powdered compositions according to the invention comprise as the non-ionic film-forming and/or non-ionic setting polymer (c) at least one copolymer (n1) that comprises at least one structural unit according to Formula (M-I) and at least one structural unit according to Formula (M-VII) and at least one structural unit according to Formula (M-VIII):

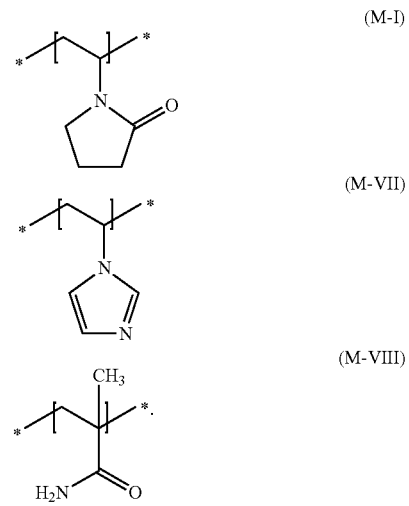

Also in this regard it is particularly preferred when these copolymers comprise, in addition to polymer units that result from the incorporation of the cited structural units in accordance with Formula (M1-a), (I), (VII) and (VIII) into the copolymer, maximum 5 wt %, preferably maximum 1 wt % of polymer units that trace back to the incorporation of other monomers. The copolymers (n1) are preferably exclusively constituted from structural units of Formula (M1-a), (I), (VII) and (VIII) and can be described by the general Formula (Poly4):

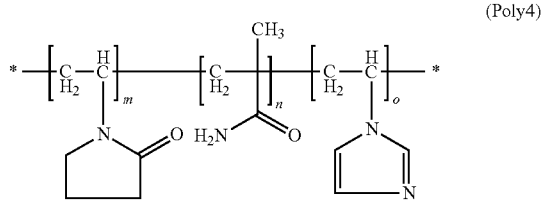

wherein each of the indices m, n, o and p vary according to the molecular mass of the polymer and are not intended to mean to portray block copolymers. In fact, structural units of Formula (I), (VII) and (VIII) can be statistically distributed in the molecule.

A particularly preferred polymer, here, is selected from the polymers of the INCI name VP/Methacrylamide/Vinyl Imidazole Copolymer which are available for example from BASF SE under the trade name Luviset® Clear.

Those powdered compositions are again inventively suitable that comprise at least one non-ionic film-forming and/or non-ionic setting polymer, containing at least one structural unit of the Formula (M-I) and at least one structural unit of the Formula (M-III):

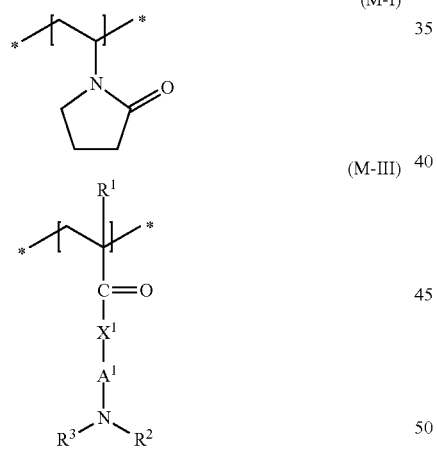

wherein, $R^1$ stands for a hydrogen atom or a methyl group; $X^1$ stands for an oxygen atom or an NH group; $A^1$ stands for an ethane-1,2-diyl, propane-1,3-diyl or butane-1,4-diyl group; and $R^2$ and $R^3$ stand independently of one another for a ($C_1$ to $C_4$) alkyl group.

In this regard it is particularly preferred when the above non-ionic film-forming and/or non-ionic setting polymer is selected from at least one polymer that fulfils at least one or more of the following criteria: $R^1$ denotes a methyl group; $X^1$ denotes an NH group; $A^1$ stands for ethane-1,2-diyl or propane-1,3-diyl; and $R^2$ and $R^3$, stand independently of one another for methyl or ethyl, (particularly preferably for methyl.

The nonionic film-forming and/or non-ionic setting polymer of this embodiment particularly preferably concerns at least one polymer that contains at least one structural unit of the Formula (M-I) and at least one structural unit of the Formula (M-III-8):

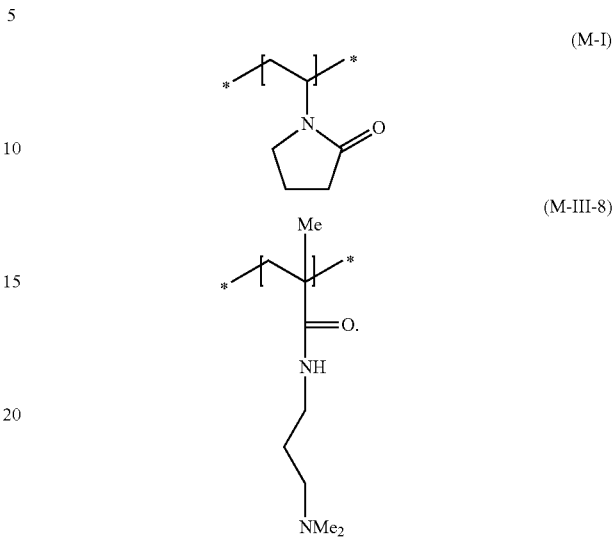

A quite particularly preferred non-ionic film-forming and/or non-ionic setting polymer of this embodiment is a copolymer of N-vinyl pyrrolidone and N,N-dimethylaminiopropyl-methacrylamide that is sold for example with the INCI name VP/DMAPA Acrylates Copolymer e.g. under the trade name Styleze® CC 10 by ISP.

Agents for treating keratin-containing fibers, especially human hair, are preferred that comprise in a cosmetically acceptable carrier:

(a) at least one copolymer containing at least one structural unit of Formula (I) and at least one structural unit of Formula (II):

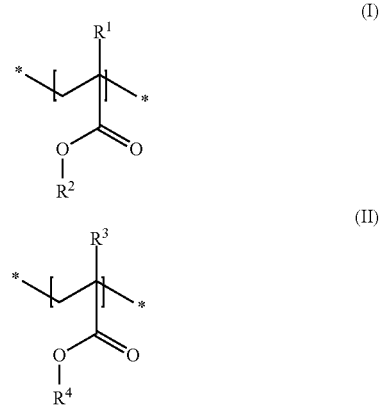

wherein $R^1$ and $R^3$ independently of one another denote a hydrogen atom or a methyl group; $R^2$ denotes a dihydroxypropyl group (especially for 2,3-dihydroxypropyl) that can be substituted with a glyceryl group or an oligoglyceryl group of 2 to 10 glyceryl units; $R^4$ denotes a hydrogen atom or a ($C_1$ to $C_4$) alkyl group;

(b) at least one copolymer of maleic anhydride and methyl vinyl ether as the film-forming and/or setting polymer; and (c) at least one ester oil.

Agents for treating keratin-containing fibers, especially human hair, are preferred that comprise in a cosmetically acceptable carrier:
(a) at least one copolymer containing at least one structural unit of Formula (I) and at least one structural unit of Formula (II):

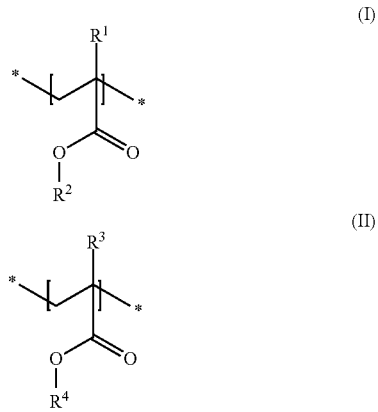

wherein $R^1$ and $R^3$ independently of one another denote a hydrogen atom or a methyl group; $R^2$ denotes a dihydroxypropyl group (especially for 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acids containing 2 to 8 carbon atoms, especially from N-vinyl pyrrolidone and vinyl acetate, copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof; and
(c) at least one ester oil.

Agents for treating keratin-containing fibers, especially human hair, are preferred that comprise in a cosmetically acceptable carrier:
(a) at least one copolymer of glyceryl acrylate and acrylic acid;
(b) at least one copolymer of maleic anhydride and methyl vinyl ether as the film-forming and/or setting polymer; and
(c) at least one ester oil.

Agents for treating keratin-containing fibers, especially human hair, are preferred that comprise in a cosmetically acceptable carrier:
(a) at least one copolymer of glyceryl acrylate and acrylic acid;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid having 2 to 18 carbon atoms, (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof; and
(c) at least one ester oil.

In the context of a preferred embodiment, the inventive compositions comprise as the film-forming and/or setting polymer at least one film-forming anionic and/or setting anionic polymer.

According to the invention, an anionic polymer is understood to mean a polymer that in a protic solvent under standard conditions carries structural units containing anionic groups that have to be compensated by counter ions in order to maintain electroneutrality and that does not possess any structural units containing permanently cationic or cationizable groups. Anionic groups include carboxylic acid and sulfonic acid groups. The polymers differ from the copolymers of the component (a).

The agent according to the invention preferably comprises the anionic, film-forming and/or anionic, setting polymers in an amount of 0.1 wt % to 20.0 wt %, particularly preferably 0.2 wt % to 15.0 wt %, and quite particularly preferably 0.5 wt % to 10.0 wt %, each based on the weight of the agent according to the invention.

It is inventively preferred when the film-forming anionic and/or setting anionic polymer comprises at least one structural unit of the Formula (S-1) that is selected from at least one structural unit of the Formulas (S1-1) to (S1-3):

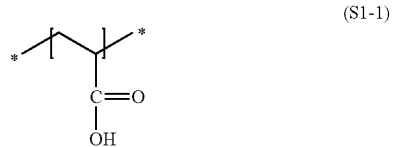

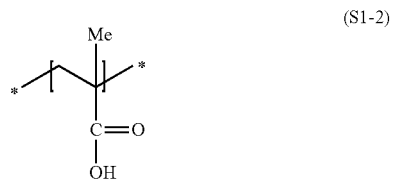

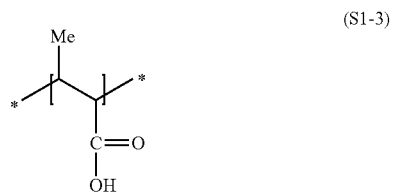

It is inventively preferred when the film-forming anionic and/or setting anionic polymer comprises, in addition to at least one structural unit of the Formulas (S1-1) to (S1-3), at least one structural unit of the Formulas (S2) that is selected from at least one structural unit of the Formulas (S2-1) to (S2-8):

(S2-1) 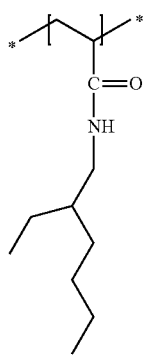

(S2-2) 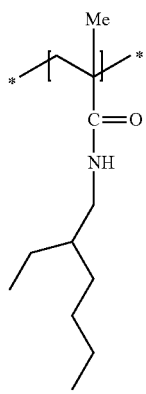

(S2-3) 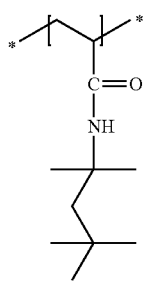

(S2-4) 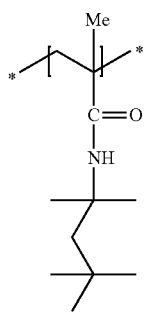

(S2-5) 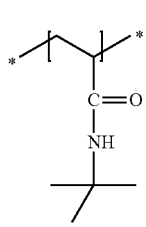

(S2-6) 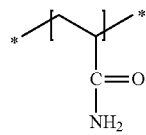

(S2-7) 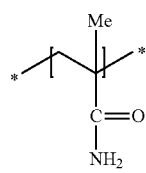

(S2-8) 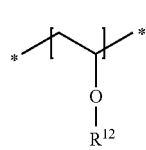

wherein $R^{12}$ denotes a ($C_2$ to $C_{12}$) acyl group (especially acetyl or neodecanoyl).

In the context of a preferred embodiment, those agents are inventively preferred which as in the form of particles of the present film-forming and/or setting polymer comprise at least one polymer that comprises at least one structural unit of the Formula (S1-3) and at least one structural unit of the Formula (S2-8):

(S1-3) 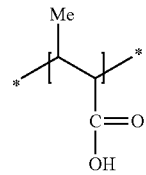

(S2-8) 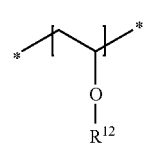

wherein $R^{12}$ denotes a ($C_2$ to $C_{12}$) acyl group (especially acetyl or neodecanoyl).

Particularly preferred polymers of this type are selected from at least one polymer from the group consisting of copolymers of vinyl acetate and crotonic acid, copolymers of vinyl propionate and crotonic acid, copolymers of vinyl neodecanoate, vinyl acetate and crotonic acid, and mixtures thereof.

Copolymers of this type are provided for example by Clariant under the trade name Aristoflex A 60 (INCI name: VA/Crotonates Copolymer) in an isopropanol-water mixture (60 wt. % active substance), by BASF under the trade name Luviset CA 66 (vinyl acetate/crotonic acid copolymer 90:10, INCI name VA/Crotonates Copolymer, by National Starch under the trade name Resyn 28-2942 or Resyn 28-2930 (INCI name: VA/Crotonates/Vinyl Neodecanoate Copolymer).

In the context of a preferred embodiment, those powdered compositions according to the invention are inventively preferred which as the anionic film-forming and/or the anionic setting polymer comprise at least one polymer that comprises at least one structural unit of the Formula (S1-1) and at least one structural unit of the Formula (S2-5):

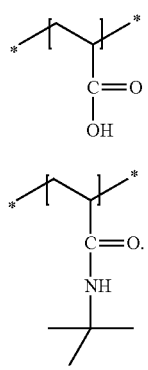

(S1-5)

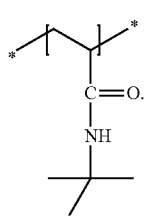

(S2-5)

Here, it is again particularly preferred when the film-forming and/or the setting polymer that is in the form of particles additionally comprises, in addition to the above structural units of Formulas (S1-1), (S2-5), at least one structural unit of the Formula (S3):

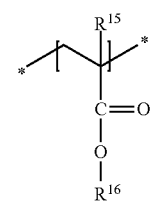

(S3)

wherein $R^{15}$ denotes a hydrogen atom or a methyl group; and $R^{16}$ denotes a ($C_1$ to $C_4$) alkyl group (in particular a methyl group or an ethyl group).

Particularly preferred polymers of this type are selected from at least one polymer of the group consisting of copolymers of acrylic acid and ethyl acrylate and N-tert-butylacrylamide. Such copolymers are for example provided by BASF under the trade name Ultrahold Strang (INCI name: Acrylates/t-Butylacrylamide Copolymer, white, pourable granulate) or Ultrahold® 8 (INCI name: Acrylates/t-Butylacrylamide Copolymer, white, pourable granulate).

In the context of a further embodiment, the inventive powdered compositions comprise as the film-forming and/or setting polymer at least one amphoteric film-forming and/or amphoteric setting polymer.

According to the invention, an amphoteric polymer is understood to mean a polymer that in a protic solvent under standard conditions carries structural units containing anionic groups that have to be compensated by counter ions in order to maintain electroneutrality and additionally structural units containing groups that are cationizable by protonation, but are free of permanently cationized groups. Anionic groups include carboxylic acid and sulfonic acid groups. Permanently cationized nitrogen atoms are understood to mean those nitrogen atoms that carry a positive charge and thereby form a quaternary ammonium compound.

The powdered composition according to the invention preferably comprises the amphoteric, film-forming and/or amphoteric, setting polymers in an amount of 0.1 wt % to 20.0 wt %, particularly preferably 0.2 wt % to 15.0 wt %, and quite particularly preferably 0.5 wt % to 5.0 wt %, each based on the weight of the composition according to the invention.

It is inventively suitable when the film-forming amphoteric and/or setting amphoteric polymer comprises at least one structural unit of Formula (S1) that is selected from at least one structural unit of the Formulas (S1-1) to (S1-3):

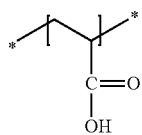

(S1-1)

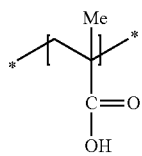

(S1-2)

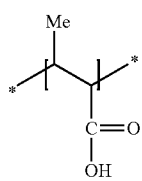

(S1-3)

It is inventively suitable when the film-forming amphoteric and/or setting amphoteric polymer comprises, in addition to at least one structural unit of the Formulas (S1-1) to (S1-3), at least one structural unit of the Formulas (S2) that is selected from at least one structural unit of the Formulas (S2-9) to (S2-15):

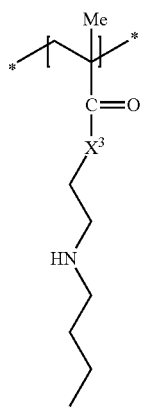

(S2-9)

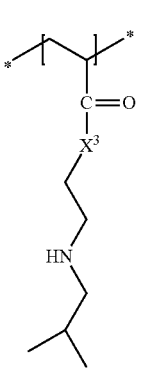

(S2-10)

(S2-11) 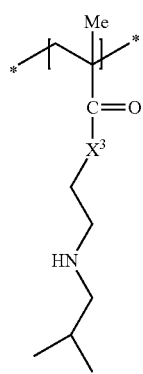
(S2-12) 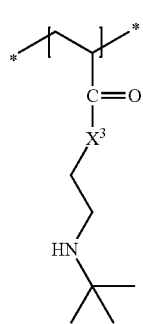
(S2-13) 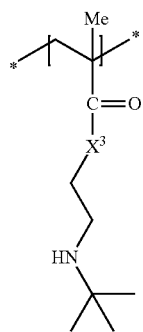
(S2-14) 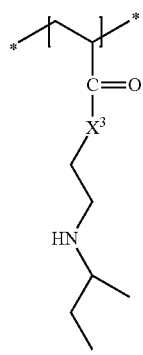
(S2-15) 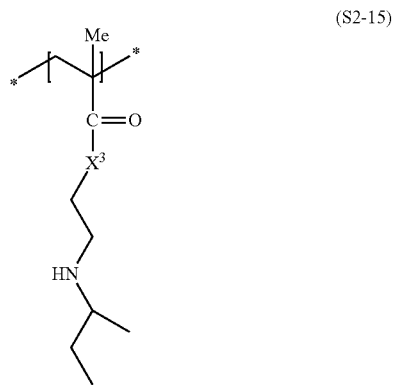
wherein $X^3$ denotes an oxygen atom or an NH group.
It is again inventively suitable when the film-forming amphoteric and/or setting amphoteric polymer comprises, in addition to at least one structural unit of the Formulas (S1-1) to (S1-3) and at least one structural unit of the Formulas (S2-9) to (S2-15) additionally at least one structural unit of the Formulas (S2-1) to (S2-8):
(S2-1) 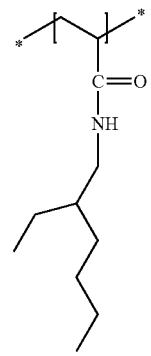
(S2-2) 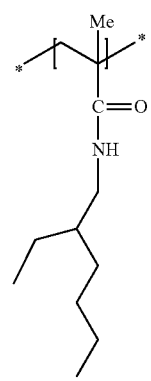

-continued

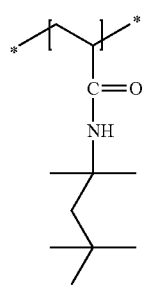
(S2-3)

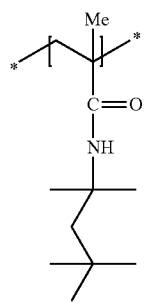
(S2-4)

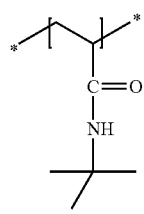
(S2-5)

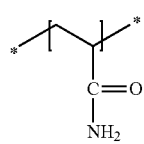
(S2-6)

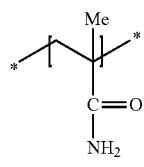
(S2-7)

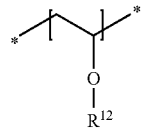
(S2-8)

Wherein $R^{12}$ denotes a ($C_2$ to $C_{12}$) acyl group (especially acetyl or neodecanoyl).

In the context of another embodiment of the invention, the powdered composition according to the invention comprises at least one film-forming amphoteric and/or setting amphoteric polymer that comprises at least one structural unit of the Formula (S1-1), at least one structural unit of the Formula (S2-3) and at least one structural unit of the Formula (S2-16) (in particular selected from the group consisting of the above Formulas (S2-5) to (S2-12) with the proviso that $X^3$ stands for an oxygen atom):

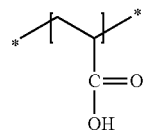
(S1-1)

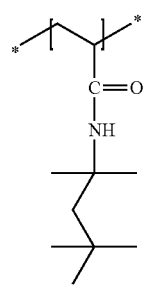
(S2-3)

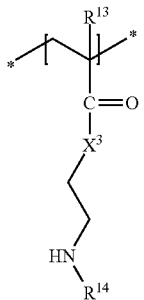
(S2-16)

wherein $X^3$ denotes an oxygen atom or an NH group; $R^{13}$ denotes a hydrogen atom or a methyl group; and $R^{14}$ denotes an alkyl group containing 4 carbon atoms (in particular n-butyl, sec-butyl, iso-butyl, or tert-butyl).

It is again particularly suitable when the film-forming amphoteric and/or setting amphoteric polymer comprises, in addition to the above structural units of the Formulas (S1-1), (S2-3) and (S2-16) at least one structural unit of the Formula (S3):

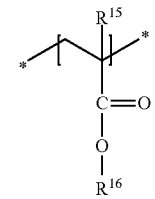
(S3)

wherein $R^{15}$ stands for a hydrogen atom or a methyl group; and $R^{16}$ stands for a ($C_1$ to $C_4$) alkyl group (in particular a methyl group or an ethyl group).

Preferred polymers of this type are selected from the group consisting of copolymers of acrylic acid, ($C_1$ to $C_4$) alkyl acrylate, N—($C_4$ alkyl)aminoethyl methacrylate, N—($C_8$ alkyl)acrylamide, and mixtures thereof.

An example of a film-forming and/or setting polymer that can be particularly preferably used in the context of this embodiment is the polymer with the INCI name Octylacrylamide/Acrylates/Butylaminoethylmethacrylate Copolymer, available under the trade name Amphomer® from the National Starch Company.

The agent according to the invention comprise at least one ester oil as component (c), together with the copolymer of the component (a) and the film-forming and/or setting polymer of the component (b).

Ester oils according to the invention exhibit a melting point of less than 30° C. at a pressure of 1013 bar and possess at least one alkyloxycarbonyl group in the molecule.

Preferred agents according to the invention comprise the ester oils in an amount of 0.5 to 30 wt %, particularly preferably 1 to 20 wt %, each based on the weight of the agent.

Preferred ester oils are selected from monocarboxylic acid esters of ($C_3$ to $C_{20}$) alcohols and/or dialkyl carbonates and/or diesters of ($C_3$ to $C_{20}$) alcohols with alpha, omega-($C_4$ to $C_8$) carboxylic acids.

Those agents are inventively preferred and suitable, in which the ester oil is selected from at least one compound of the Formula (III) and/or the Formula (IV):

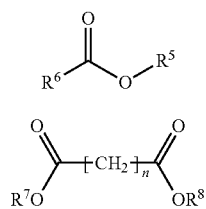

wherein $R^6$ denotes a linear ($C_3$ to $C_{17}$) alkyl group, a branched ($C_3$ to $C_{17}$) alkyl group, a ($C_2$ to $C_6$) hydroxyalkyl group, a linear ($C_3$ to $C_{18}$) alkoxy group, or a branched ($C_3$ to $C_{18}$) alkoxy group; $R^5$ denotes a linear ($C_3$ to $C_{20}$) alkyl group or branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6.

The inventive effects are particularly pronounced when the agent comprises as the ester oil at least one compound selected from diisopropyl adipate, di-n-butyl adipate, dioctyl maleate, tridecyl neopentanoate (e.g. Ceraphyl® 55 from the ISP company), decyl oleate (e.g. Ceraphyl® 140 from the ISP company), isostearyl neopentanoate (e.g. Ceraphyl® 375 from the ISP company), isocetyl stearate (e.g. Ceraphyl® 494 from the ISP company), 2-octyldodecyl stearate (e.g. Ceraphyl® ODS from the ISP company), isopropyl myristat, isononanoic acid $C_{16-18}$ alkyl ester, 2-ethylhexyl palmitate, stearic acid 2-ethylhexyl ester, cetyl oleate, coco fatty alcohol caprinate/caprylate, n-butyl stearate, oleyl erucate, isopropyl palmitate, oleyl oleate, lauric acid hexyl ester, cetearyl isononanoate, lauryl lactate (e.g. Ceraphyl® 31 from the ISP company), ($C_{12}$ to $C_{15}$) alkyl lactate (e.g. Ceraphyl® 41 from the ISP company), dihexyl carbonate, dioctyl carbonate (e.g. Cetiol® CC from the Cognis company), dodecyl carbonate.

Very good results were obtained with an ester oil combination comprising: (d) at least one ester oil of the Formula (III) and/or of the Formula (IV),

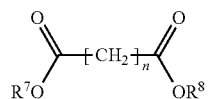

wherein $R^6$ denotes a linear ($C_3$ to $C_{17}$) alkyl group, a branched ($C_3$ to $C_{17}$) alkyl group or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n stands for a whole number from 2 to 6; and (c2) at least one ester oil of the Formula (V):

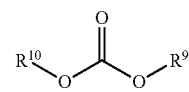

wherein $R^9$ and $R^{10}$ denote independently of one another a linear ($C_4$ to $C_{18}$) alkyl group or a branched ($C_4$ to $C_{18}$) alkyl group.

Preferred agents for treating keratin-containing fibers such as human hair, are comprise, in a cosmetically acceptable carrier:

(a) at least one copolymer containing at least one structural unit of Formula (I) and at least one structural unit of Formula (II):

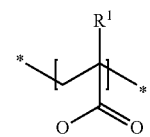

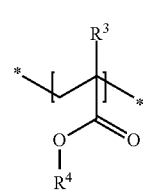

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; $R^4$ denotes a hydrogen atom or a ($C_1$ to $C_4$) alkyl group;

(b) at least one copolymer of maleic anhydride and methyl vinyl ether as the film-forming and/or setting polymer;

(c1) at least one ester oil of the Formula (III) and/or the Formula (IV):

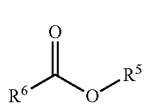

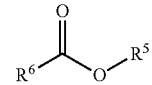

-continued

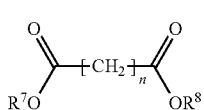
(IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6; and (c2) at least one ester oil of the Formula (V):

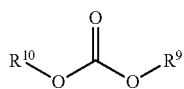
(V)

wherein $R^9$ and $R^{10}$ denote independently of one another a linear ($C_4$ to $C_{18}$) alkyl group or a branched ($C_4$ to $C_{18}$) alkyl group.

Preferred agents for treating keratin-containing fibers, especially human hair, comprise in a cosmetically acceptable carrier:

(a) at least one copolymer containing at least one structural unit of Formula (I) and at least one structural unit of Formula (II):

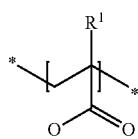
(I)

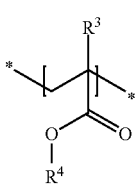
(II)

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;

(b1) at least one copolymer of maleic anhydride and methyl vinyl ether;

(b2) at least one non-ionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;

(c1) at least one ester oil of the Formula (III) and/or the Formula (IV):

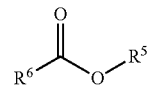
(III)

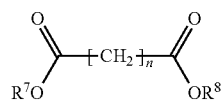
(IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denotes independently of one another a linear ($C_3$ to $C_m$) alkyl group or a branched ($C_3$ to $C_{10}$) alkyl group; and n denotes a whole number from 2 to 6; and (c2) at least one ester oil of the Formula (V):

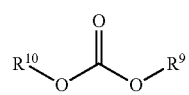
(V)

wherein $R^9$ and $R^{10}$ denote independently of one another a linear ($C_4$ to $C_{18}$) alkyl group or a branched ($C_4$ to $C_{18}$) alkyl group.

Preferred agents for treating keratin-containing fibers, especially human hair, comprise in a cosmetically acceptable carrier:

(a) at least one copolymer of glyceryl acrylate and acrylic acid;

(b) at least one copolymer of maleic anhydride and methyl vinyl ether as the film-forming and/or setting polymer;

(c1) at least one ester oil of the Formula (III) and/or the Formula (IV):

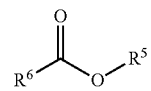
(III)

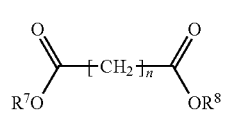
(IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6; and (c2) at least one ester oil of Formula (V):

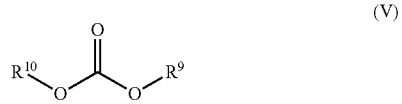

wherein $R^9$ and $R^{10}$ denote independently of one another a linear ($C_4$ to $C_{18}$) alkyl group or a branched ($C_4$ to $C_{18}$) alkyl group.

Preferred agents for treating keratin-containing fibers, especially human hair, comprise in a cosmetically acceptable carrier:
(a) at least one copolymer of glyceryl acrylate and acrylic acid;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;
(c1) at least one ester oil of the Formula (III) and/or the Formula (IV):

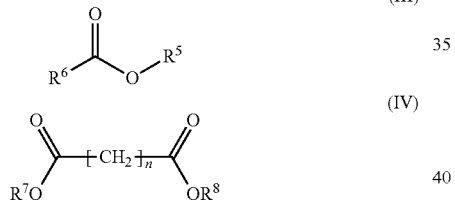

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6; and
(c2) at least one ester oil of Formula (V):

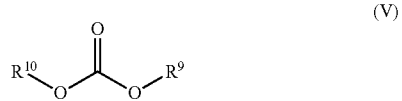

wherein $R^9$ and $R^{10}$ denote independently of one another a linear ($C_4$ to $C_{18}$) alkyl group or a branched ($C_4$ to $C_{18}$) alkyl group.

Here, each of the previously cited preferred ester oils of the component (c) and/or the preferred added quantities are also considered as preferred.

At least one ester oil of linear or branched ($C_3$-$C_{20}$) monocarboxylic acids with linear or branched ($C_3$-$C_{20}$) alcohols serves as a particularly preferred ester oil of the component (c1).

Di(n-octyl)carbonate serves as a particularly preferred ester oil of the component (c2).

It is inventively preferred when the agent additionally comprises at least one ($C_2$ to $C_6$) polyol. ($C_2$ to $C_6$) polyols according to the invention comprise at least 2 hydroxyl groups. It is inventively preferred when the ($C_2$ to $C_6$) polyol is a liquid at 25° C. under a pressure of 1 atm.

The polyols are preferably selected from at least one polyol from the group consisting of glycerin, 1,2-ethylene glycol, 1,2-propylene glycol, butane-2,3-diol, 2-methyl-2,4-butane diol, 2-methyl-2,4-pentane diol, 1,5-pentane diol, 2-ethyl-1,3-hexane diol, 1,2,4-pentane triol, 1,3,4-pentane diol, 1,3,5-pentane triol, and mixtures thereof. The agents according to the invention more preferably comprise glycerine as the polyol.

In the context of the invention, preferred agents comprise the ($C_2$ to $C_6$) polyols (preferably glycerine) in an amount of 0.5 wt % to 15.0 wt %, particularly preferably 1.0 wt % to 10.0 wt %, each based on the weight of the agent.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

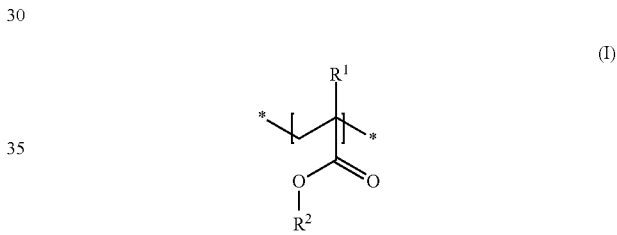

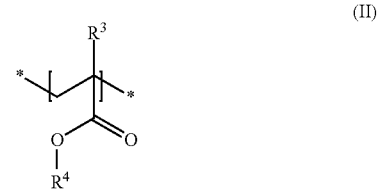

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b) film-forming and/or setting polymer;
(c) at least one ester oil; and
(d) glycerin.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

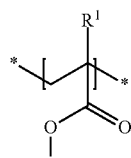

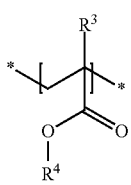

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b) at least one copolymer of maleic anhydride and methyl vinyl ether as the film-forming and/or setting polymer;
(c) at least one ester oil; and
(d) glycerin.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

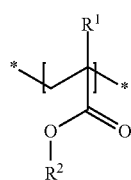

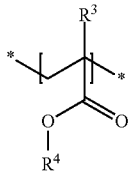

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;
(c) at least one ester oil; and
(d) glycerin.

Preferably, the agents for treating keratin-containing fibers, especially human hair, comprise in a cosmetically acceptable carrier:
(a) at least one copolymer of glyceryl acrylate and acrylic acid;
(b) at least one copolymer of maleic anhydride and methyl vinyl ether as the film-forming and/or setting polymer;
(c) at least one ester oil; and
(d) glycerin.

Preferred agents useful for treating keratin-containing fibers, especially human hair, comprise within a cosmetically acceptable carrier:
(a) at least one glyceryl acrylate and acrylic acid copolymer;
(b1) at least one maleic anhydride and methyl vinyl ether copolymer;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;
(c) at least one ester oil; and
(d) glycerin.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b) at least one film-forming and/or setting polymer;

(c1) at least one ester oil of the Formula (III) and/or the Formula (IV):

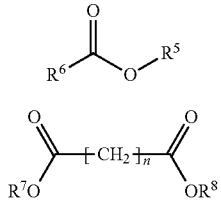

(III)

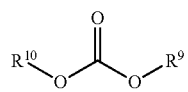

(IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

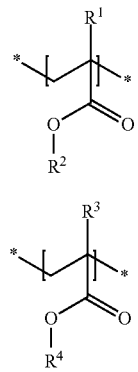

(V)

wherein $R^9$ and $R^{10}$ denote independently of one another a linear ($C_4$ to $C_{18}$) alkyl group or a branched ($C_4$ to $C_{18}$) alkyl group; and
(d) glycerin.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

(I)

(II)

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b) at least one copolymer of maleic anhydride and methyl vinyl ether as the film-forming and/or setting polymer;
(c1) at least one ester oil of the Formula (III) and/or the Formula (IV):

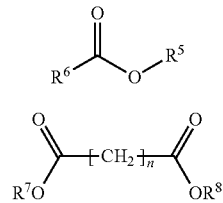

(III)

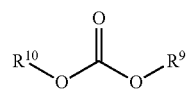

(IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

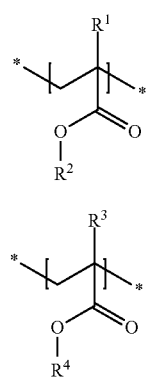

(V)

wherein $R^9$ and $R^{10}$ denote independently of one another a linear ($C_4$ to $C_{18}$) alkyl group or a branched ($C_4$ to $C_{18}$) alkyl group; and
(d) glycerin.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

(I)

(II)

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;

(c1) at least one ester oil of the Formula (III) and/or the Formula (IV):

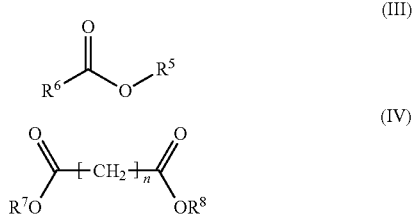

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

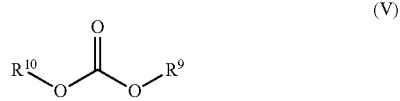

wherein $R^9$ and $R^{10}$ denote independently of one another a linear ($C_4$ to $C_{18}$) alkyl group or a branched ($C_4$ to $C_{18}$) alkyl group; and (d) glycerin.

Agents for treating keratin-containing fibers, especially human hair, are preferred that comprise in a cosmetically acceptable carrier:

(a) at least one glyceryl acrylate and acrylic acid copolymer;
(b) at least one copolymer of maleic anhydride and methyl vinyl ether as the film-forming and/or setting polymer;
(c1) at least one ester oil of the Formula (III) and/or the Formula (IV):

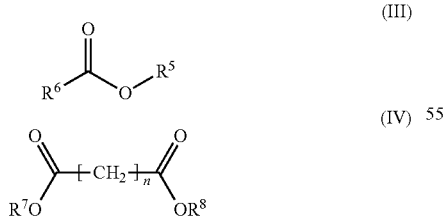

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

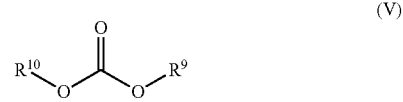

wherein $R^9$ and $R^{10}$ denote independently of one another a linear ($C_4$ to $C_{18}$) alkyl group or a branched ($C_4$ to $C_{18}$) alkyl group; and (d) glycerin.

Agents for treating keratin-containing fibers, especially human hair, are preferred that comprise in a cosmetically acceptable carrier:

(a) at least one glyceryl acrylate and acrylic acid copolymer;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;

(c1) at least one ester oil of the Formula (III) and/or the Formula (IV):

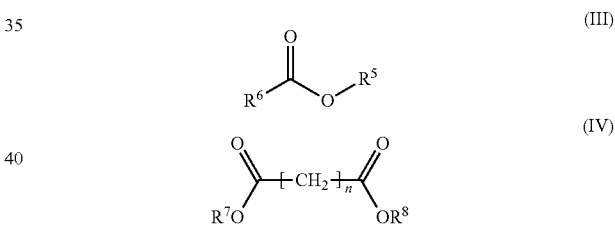

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

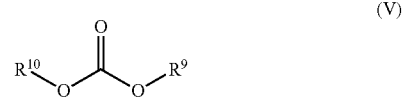

wherein $R^9$ and $R^{10}$ denote independently of one another a linear ($C_4$ to $C_{18}$) alkyl group or a branched ($C_4$ to $C_{18}$) alkyl group; and (d) glycerin.

In the context of a particularly preferred embodiment, the agent according to the invention has been thickened. Preferred agents according to the invention additionally comprise as the thickener at least one sulfonic acid polymer, containing at least one structural unit according to Formula (P-I) and at least one structural unit according to Formula (P-II):

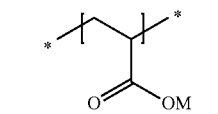
(P-I)

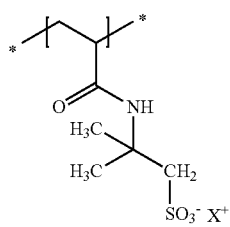
(P-II)

wherein M denotes hydrogen or sodium; and X denotes a physiologically acceptable cation.

The first monomer that is comprised in the sulfonic acid polymer is acrylic acid or sodium acrylate, i.e. the sodium salt of acrylic acid.

The second monomer that is comprised in the sulfonic acid polymer is 2-methyl-2[(1-oxo-2-propenyl)amino]-1-propanesulfonic acid (AMPS) that can be present partially or totally neutralized. $Na^+$ and $NH^{4+}$ are usually preferred as the cations.

Preferred sulfonic acid polymers can be described by the general formula:

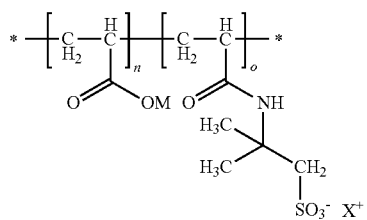

wherein each of the indices n and o vary according to the molecular mass of the polymer and are not intended to necessarily portray block copolymers. In fact, structural units of the Formulas (P-I) and (P-II) can be statistically distributed in the molecule.

Preferred sulfonic acid polymers of this type are copolymers of 2-methyl-2[(1-oxo-2-propenyl)amino]-1-propanesulfonic acid (AMPS) and sodium acrylate, which are available for example as the commercial product Simulgel® EG (INCI name: Sodium Acrylates/Sodium Acryloyldimethyl Taurate Copolymer, Isohexadecane, Polysorbate 80) from the Seppic company.

It is preferred that the cited additional sulfonic acid polymer contain at least one structural unit of the Formula (P-III, i.e. dimethylacrylamide) in addition to the structural units of the Formula (P-I) and (P-II):

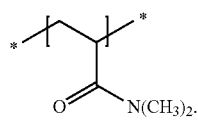
(P-III)

The preferred sulfonic acid polymers can be described by the general formula:

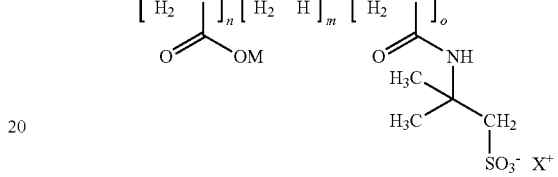

wherein each of the indices m and n and o vary according to the molecular mass of the polymer and are not intended to necessarily portray block copolymers. In fact, structural units of the Formulas (P-I), (P-II) and (P-III) can be statistically distributed in the molecule.

The monomers of the Formulas (P-I), (P-II), and (P-III) are preferably arranged within the sulfonic acid polymer in number and distribution such that the copolymer A has a molecular mass between 5 and 1000 kDa. Preferred inventive compositions comprise the copolymer(s) A having molecular masses of 10 to 750 kDa, preferably from 25 to 500 kDa, more preferably from 50 to 400 kDa and particularly from 70 to 250 kDa.

The sulfonic acid polymer preferably comprises the monomers having Formulas (P-I), (P-II) and (P-III) within specific limits. Here, inventively preferred agents comprise the sulfonic acid polymers further comprising: 10 to 90 mol %, preferably 15 to 85 mol % and especially 20 to 80 mol % of monomers of the Formula (P-I); 5 to 85 mol %, preferably 7.5 to 80 mol % and especially 10 to 60 mol % of monomers of the Formula (P-II); and, 5 to 85 mol %, preferably 10 to 80 mol % and especially 15 to 70 mol % of monomers of the Formula (P-III).

Independent of whether the agents according to the invention comprise one or more sulfonic acid polymers, it is preferred to incorporate the sulfonic acid polymers within specific quantity ranges. Here, preferred inventive agents comprise the sulfonic acid polymer(s) in an amount of 0.1 to 10 wt %, preferably 0.5 to 7.5 wt % and particularly 1 to 5 wt %, each based on the weight of the agent.

The compositions according to the invention quite particularly preferably comprise the sulfonic acid polymer in the form of an auto-inversible polymer latex, comprising an oil phase, an aqueous phase, at least one oil-in-water emulsifier and at least one branched or crosslinked polyelectrolyte (=sulfonic acid polymer) that represents a copolymer that possesses at least one monomer with a strong acid function as well as at least one additional monomer that comprises a weak acid function.

All abovementioned, preferably used inverse polymer lattices have in common that they comprise at least one oil, preferably selected from white mineral oils, squalane, isohexadecane and (optionally hydrogenated) polyisobutene, as well as at least one oil-in-water emulsifier, selected from the ethylene oxide adducts of sorbitol oleate, castor oil that if desired is hydrogenated, sorbitol laurate and lauryl alcohol, as well as additionally selected from the polyethylene oxide-free oil-in-water-emulsifier class of the $C_6$-$C_{22}$ fatty alcohol glucose ethers, in particular caprinic glucosides, caprylic glucosides, capric glucosides, lauric glucosides, myristic glucosides, cetyl glucosides, stearyl glucosides, arachidyl glucosides, behenyl glucosides, particularly preferably caprylic glucosides and capric glucosides. Accordingly, preferred compositions according to the invention are those wherein the oil phase of the inverse polymer latex comprises at least one oil, selected from white mineral oils, squalane, isohexadecane and (optionally hydrogenated) polyisobutene. Further preferred compositions according to the invention are those wherein the oil-in-water emulsifier comprised in the inverse polymer latex is selected from the ethylene oxide adducts of sorbitol oleate, castor oil that if desired is hydrogenated, sorbitol laurate and lauryl alcohol, as well as from caprylic glucosides and capric glucosides.

The inventively preferred useable thickening polymer lattices preferably have a polymer content of sulfonic acid polymer of 30-90 wt %, preferably 35-75 wt % and particularly preferably 40-60 wt %, each based on the total latex. However, the polymer content of the latex in this regard has really only a significance for the production of the composition according to the invention, e.g. with regard to the miscibility or metering. For the inventive composition itself, rather the polymer content itself is significant, based on the inventive composition (see above).

The sulfonic acid polymer is particularly preferably inventively incorporated in the form of an inverse, auto-inversible polymer latex that comprises isohexadecane as the oil phase and sorbitol monostearate as the emulsifier in addition to the sulfonic acid polymer.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

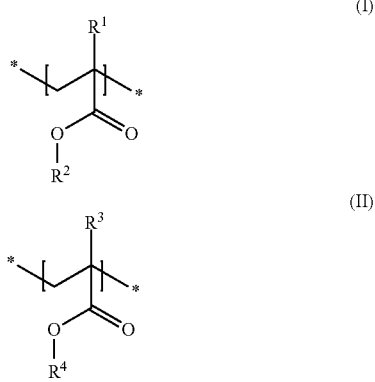

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b) film-forming and/or setting polymer;
(c) at least one ester oil;
(d) glycerin; and
(e) at least one sulfonic acid polymer, containing at least one structural unit according to Formula (P-I) and at least one structural unit according to Formula (P-II):

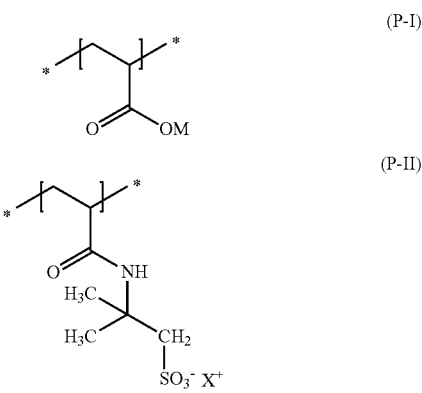

wherein M denotes hydrogen or sodium and X denotes a physiologically acceptable cation.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

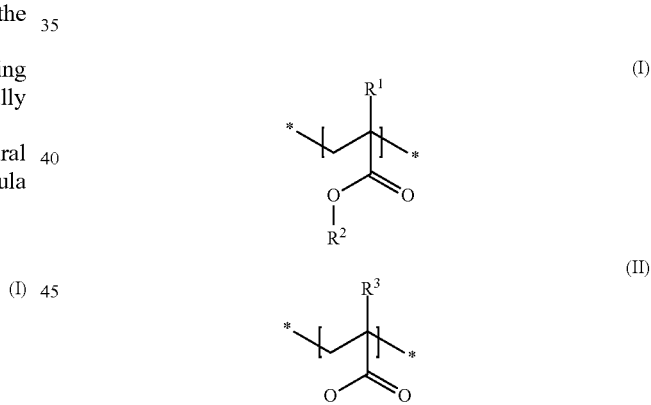

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b) at least one copolymer of maleic anhydride and methyl vinyl ether as the film-forming and/or setting polymer;
(c) at least one ester oil;
(d) glycerin; and
(e) at least one sulfonic acid polymer, containing at least one structural unit according to Formula (P-I) and at least one structural unit according to Formula (P-II):

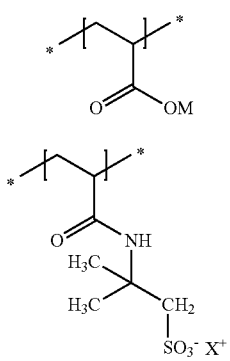 (P-I)

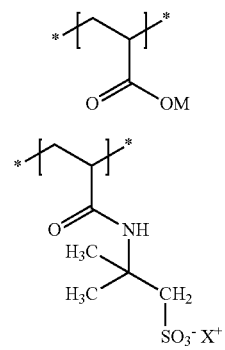 (P-I)

(P-II)

(P-II)

wherein M denotes hydrogen or sodium and X denotes a physiologically acceptable cation.

Preferably, the agents for treating keratin-containing fibers, especially human hair, comprise in a cosmetically acceptable carrier:
(a) at least one copolymer containing at least one structural unit of Formula (I) and at least one structural unit of Formula (II):

wherein M denotes hydrogen or sodium and X denotes a physiologically acceptable cation.

Agents for treating keratin-containing fibers, especially human hair, are preferred that comprise in a cosmetically acceptable carrier:
(a) at least one glyceryl acrylate and acrylic acid copolymer;
(b) at least one copolymer of maleic anhydride and methyl vinyl ether as the film-forming and/or setting polymer;
(c) at least one ester oil;
(d) glycerin; and
(e) at least one sulfonic acid polymer, containing at least one structural unit according to Formula (P-I) and at least one structural unit according to Formula (P-II):

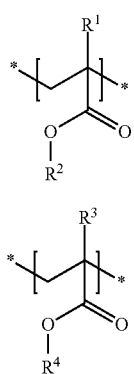 (I)

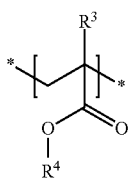 (II)

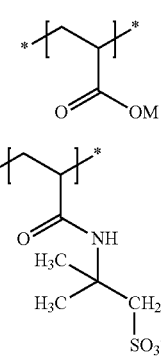 (P-I)

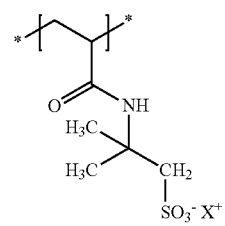 (P-II)

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;
(c) at least one ester oil;
(d) glycerin; and
(e) at least one sulfonic acid polymer, containing at least one structural unit according to Formula (P-I) and at least one structural unit according to Formula (P-II):

wherein M denotes hydrogen or sodium and X denotes a physiologically acceptable cation.

Agents for treating keratin-containing fibers, especially human hair, are preferred that comprise in a cosmetically acceptable carrier:
(a) at least one glyceryl acrylate and acrylic acid copolymer;
(b1) at least one copolymer of maleic anhydride and methyl vinyl ether;
(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;
(c) at least one ester oil;

(d) glycerin; and (e) at least one sulfonic acid polymer, containing at least one structural unit according to Formula (P-I) and at least one structural unit according to Formula (P-II):

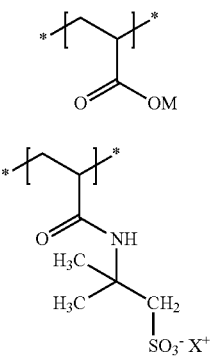

wherein M denotes hydrogen or sodium and X denotes a physiologically acceptable cation.

Preferably, the agents for treating keratin-containing fibers, especially human hair, comprise in a cosmetically acceptable carrier:

(a) at least one copolymer containing at least one structural unit of Formula (I) and at least one structural unit of Formula (II):

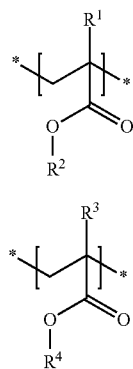

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;

(b) at least one film-forming and/or setting polymer;

(c1) at least one ester oil of the Formula (III) and/or the Formula (IV):

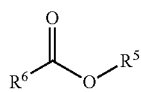

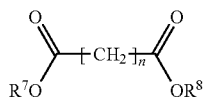

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

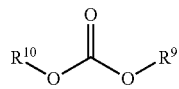

wherein $R^9$ and $R^{10}$ denote independently of one another a linear ($C_4$ to $C_{18}$) alkyl group or a branched ($C_4$ to $C_{18}$) alkyl group;

(d) glycerin; and (e) at least one sulfonic acid polymer, containing at least one structural unit according to Formula (P-I) and at least one structural unit according to Formula (P-II):

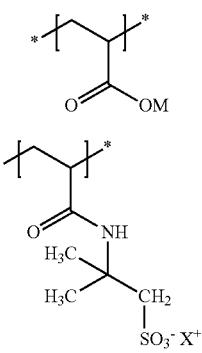

wherein M denotes hydrogen or sodium and X denotes a physiologically acceptable cation.

Preferably, the agents for treating keratin-containing fibers, especially human hair, comprise in a cosmetically acceptable carrier:

(a) at least one copolymer containing at least one structural unit of Formula (I) and at least one structural unit of Formula (II):

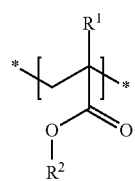

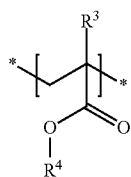 (II)

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;

(b) at least one copolymer of maleic anhydride and methyl vinyl ether as the film-forming and/or setting polymer;

(c1) at least one ester oil of the Formula (III) and/or the Formula (IV):

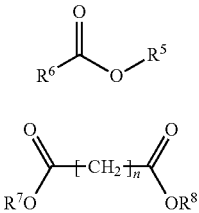

(III)

(IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

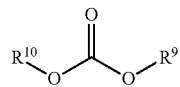 (V)

wherein $R^9$ and $R^{10}$ denote independently of one another a linear ($C_4$ to $C_{18}$) alkyl group or a branched ($C_4$ to $C_{18}$) alkyl group;

(d) glycerin; and (e) at least one sulfonic acid polymer, containing at least one structural unit according to Formula (P-I) and at least one structural unit according to Formula (P-II):

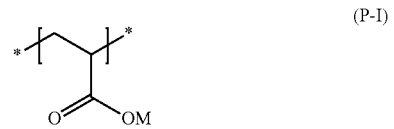 (P-I)

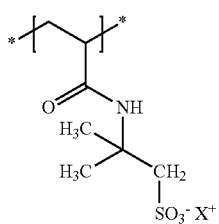 (P-II)

wherein M denotes hydrogen or sodium and X denotes a physiologically acceptable cation.

Preferably, the agents for treating keratin-containing fibers, especially human hair, comprise in a cosmetically acceptable carrier:

(a) at least one copolymer containing at least one structural unit of Formula (I) and at least one structural unit of Formula (II):

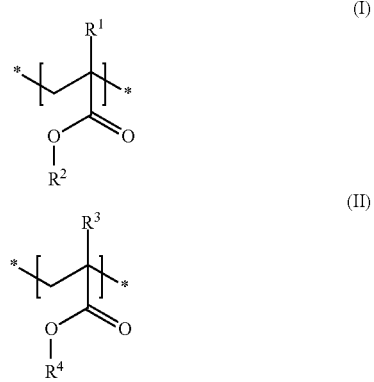

(I)

(II)

wherein $R^1$ and $R^3$ independently of one another denote a hydrogen atom or a methyl group; $R^2$ denotes a dihydroxypropyl group (especially 2,3-dihydroxypropyl) that can be substituted with a glyceryl group or an oligoglyceryl group of 2 to 10 glyceryl units; and $R^4$ denotes a hydrogen atom or a ($C_1$ to $C_4$) alkyl group;

(b1) at least one copolymer of maleic anhydride and methyl vinyl ether;

(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;

(c1) at least one ester oil of the Formula (III) and/or Formula (IV):

 (III)

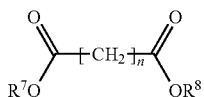 (IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

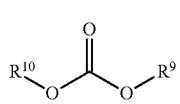 (V)

wherein $R^9$ and $R^{10}$ denote independently of one another a linear ($C_4$ to $C_{18}$) alkyl group or a branched ($C_4$ to $C_{18}$) alkyl group;

(d) glycerin; and (e) at least one sulfonic acid polymer, containing at least one structural unit according to Formula (P-I) and at least one structural unit according to Formula (P-II):

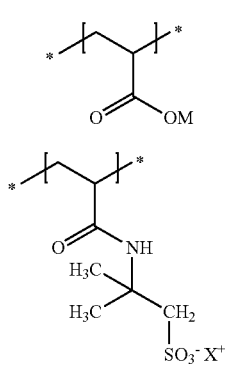 (P-I)

(P-II)

wherein M denotes hydrogen or sodium and X denotes a physiologically acceptable cation.

Preferred agents for treating keratin-containing fibers, especially human hair, comprise in a cosmetically acceptable carrier:

(a) at least one copolymer of glyceryl acrylate and acrylic acid;

(b) at least one copolymer of maleic anhydride and methyl vinyl ether as the film-forming and/or setting polymer;

(c1) at least one ester oil of the Formula (III) and/or the Formula (IV):

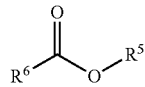 (III)

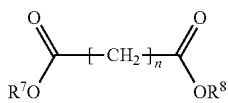 (IV)

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;

(c2) at least one ester oil of Formula (V):

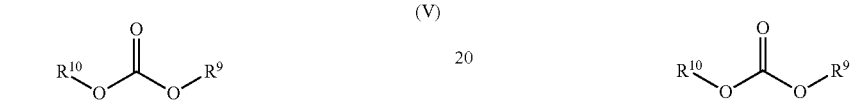 (V)

wherein $R^9$ and $R^{10}$ denote independently of one another a linear ($C_4$ to $C_{18}$) alkyl group or a branched ($C_4$ to $C_{18}$) alkyl group;

(d) glycerin; and (e) at least one sulfonic acid polymer, containing at least one structural unit according to Formula (P-I) and at least one structural unit according to Formula (P-II):

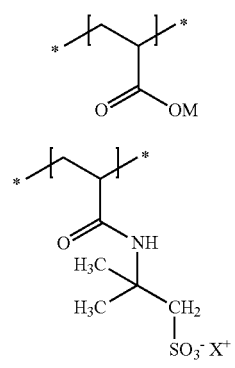 (P-I)

(P-II)

wherein M denotes hydrogen or sodium and X denotes a physiologically acceptable cation.

Preferred agents useful for treating keratin-containing fibers, especially human hair, comprise within a cosmetically acceptable carrier:

(a) at least one glyceryl acrylate and acrylic acid copolymer;

(b1) at least one maleic anhydride and methyl vinyl ether copolymer;

(b2) at least one nonionic film-forming and/or non-ionic setting polymer selected from the group consisting of polyvinyl pyrrolidone, copolymers of N-vinyl pyrrolidone and vinyl esters of carboxylic acid with 2 to 18 carbon atoms (in particular N-vinyl pyrrolidone and vinyl acetate), copolymers of N-vinyl pyrrolidone and N-vinyl imidazole and methacrylamide, copolymers of N-vinyl pyrrolidone and N-vinyl imidazole and acrylamide, copolymers of N-vinyl pyrrolidone with N,N-di($C_1$ to $C_4$) alkylamino ($C_2$ to $C_4$) alkylacrylamide, copolymers of N-vinyl pyrrolidone with N,N-di($C_1$ to $C_4$) alkylamino ($C_2$ to $C_4$) alkylacrylamide, and mixtures thereof;

(c1) at least one ester oil of the Formula (III) and/or the Formula (IV):

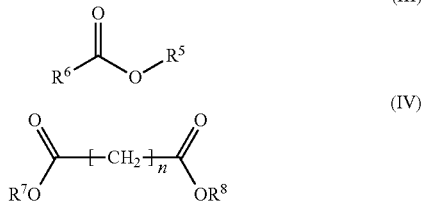

wherein $R^6$ denotes a linear ($C_3$ to $C_{17}$) alkyl group, a branched ($C_3$ to $C_{17}$) alkyl group, or a ($C_2$ to $C_6$) hydroxyalkyl group; $R^5$ denotes a linear ($C_3$ to $C_{20}$) alkyl group, branched ($C_3$ to $C_{20}$) alkyl group; $R^7$ and $R^8$ denote independently of one another a linear ($C_3$ to $C_{10}$) alkyl group or a branched ($C_3$ to $C_{10}$) alkyl group; and n denotes a whole number from 2 to 6;
(c2) at least one ester oil of Formula (V):

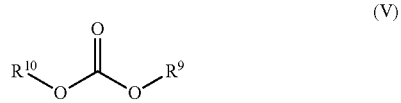

wherein $R^9$ and $R^{10}$ denote independently of one another a linear ($C_4$ to $C_{18}$) alkyl group or a branched ($C_4$ to $C_{18}$) alkyl group;
(d) glycerin; and
(e) at least one sulfonic acid polymer, containing at least one structural unit according to Formula (P-I) and at least one structural unit according to Formula (P-II):

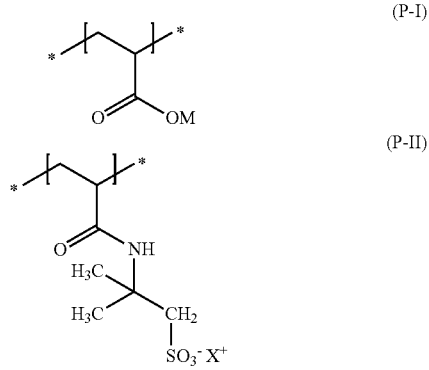

wherein M denotes hydrogen or sodium and X denotes a physiologically acceptable cation.

In this regard, the preferred embodiments of the sulfonic acid polymer of the component (e) as well as the preferred added quantities are again preferred.

The agents according to the invention can additionally comprise at least one surfactant, wherein in principal, non-ionic, anionic, cationic, ampholytic surfactants are suitable. The group of the ampholytic or also amphoteric surfactants includes zwitterionic surfactants and ampholytes. According to the invention, the surfactants can already have an emulsifying action.

The agent according to the invention preferably comprises the additional surfactants in an amount of 0.01 wt % to 5 wt %, particularly preferably 0.05 wt % to 0.5 wt %, each based on the weight of the agent.

Nonionic surfactants may comprise a polyol group, a polyalkylene glycol ether group, or a combination of polyol ether groups and polyglycol ether groups as the hydrophilic group. Exemplary compounds of this type include, but are not limited to: addition products of 2 to 100 moles ethylene oxide and/or 1 to 5 moles propylene oxide to linear and branched fatty alcohols containing 8 to 30 carbon atoms, to fatty acids containing 8 to 30 carbon atoms and to alkyl phenols containing 8 to 15 carbon atoms in the alkyl group; methyl or $C_2$-$C_6$ alkyl group end blocked addition products of 2 to 50 moles ethylene oxide and/or 1 to 5 moles propylene oxide to linear and branched fatty alcohols with 8 to 30 carbon atoms, to fatty acids with 8 to 30 carbon atoms and to alkyl phenols with 8 to 15 carbon atoms in the alkyl group, such as, for example, the commercially available types Dehydrol® LS, Dehydrol® LT (Cognis); $C_{12}$-$C_{30}$ fatty acid mono- and diesters of addition products of 1 to 30 moles ethylene oxide to glycerin; addition products of 5 to 60 moles ethylene oxide to castor oil and hydrogenated castor oil, polyol esters of fatty acids, such as, for example, the commercial product Hydagen® HSP (Cognis) or Sovermol types (Cognis); alkoxylated triglycerides; alkoxylated fatty acid alkyl esters of the Formula (E4-I), $R^1CO$—$(OCH_2CHR^2)_wOR^3$, wherein $R^1CO$ denotes a linear or branched, saturated and/or unsaturated acyl group containing 6 to 22 carbon atoms, $R^2$ denotes hydrogen or methyl, $R^3$ denotes linear or branched alkyl groups containing 1 to 4 carbon atoms, and w denotes numbers from 1 to 20; amine oxides; mixed hydroxy ethers, such as are described in DE-OS 1 973 8866; sorbitol esters of fatty acids and addition products of ethylene oxide to sorbitol esters of fatty acids such as e.g. the polysorbates; sugar esters of fatty acids and addition products of ethylene oxide to sugar esters of fatty acids; addition products of ethylene oxide to fatty acid alkanolamides and fatty amines; sugar surfactants of the alkyl and alkenyl oligoglycosides type according to Formula (E4-II), $R^4O$-$[G]_p$, wherein $R^4$ denotes an alkyl or alkenyl group containing 4 to 22 carbon atoms, G denotes a sugar group containing 5 or 6 carbon atoms and p denotes a number from 1 to 10.

Alkylene oxide addition products to saturated, linear fatty alcohols and fatty acids, each with 2 to 100 moles ethylene oxide per mole fatty alcohol or fatty acid, have proved to be quite particularly preferred non-ionic surfactants. Similarly, preparations with excellent properties are obtained when they comprise $C_{12}$-$C_{30}$ fatty acid mono and diesters of addition products of 1 to 30 moles ethylene oxide to glycerin and/or addition products of 5 to 60 moles ethylene oxide to castor oil and hydrogenated castor oil as the non-ionic surfactants.

For surfactants, which are represented by the addition products of ethylene oxide and/or propylene oxide to fatty alcohols or derivatives of these addition products, both products with a "normal" homologue distribution as well as those with a narrow homologue distribution may be used. The term "normal" homologue distribution is understood to mean mixtures of homologues obtained from the reaction of fatty alcohols and alkylene oxide using alkali metals, alkali metal hydroxides or alkali metal alkoxides as catalysts. On the other hand, narrow homologue distributions are obtained if e.g. hydrotalcite, alkaline earth metal salts of ether carboxylic acids, alkaline earth metal oxides, hydroxides or alkoxides are used as the catalysts. The use of products with a narrow homologue distribution can be preferred.

Suitable anionic surfactants are in principle all anionic surface-active materials suitable for use on the human body. They are characterized by a water solubilizing anionic group, such as e.g. a carboxylate, sulfate, sulfonate or phosphate group, and a lipophilic alkyl group containing about 8 to 30 carbon atoms. In addition, the molecule may comprise glycol or polyglycol ether groups, ester, ether and amide groups as well as hydroxyl groups. Suitable anionic surfactants may be used in the form of the sodium, potassium and ammonium, as well as the mono, di and trialkanolammonium salts containing 2 to 4 carbon atoms in the alkanol group.

Suitable anionic surfactants include, but are not limited to, the following:

(a) linear and branched fatty acids with 8 to 30 carbon atoms (soaps);
(b) ether carboxylic acids of the formula $R-O-(CH_2-CH_2O)_x-CH_2-COOH$, in which R is a linear alkyl group with 8 to 30 carbon atoms and $x=0$ or 1 to 16;
(c) acyl sarcosides with 8 to 24 carbon atoms in the acyl group;
(d) acyl taurides with 8 to 24 carbon atoms in the acyl group;
(e) acyl isethionates with 8 to 24 carbon atoms in the acyl group;
(f) mono- and dialkyl esters of sulfosuccinic acid with 8 to 24 carbon atoms in the alkyl group and mono-alkyl polyoxyethyl esters of sulfosuccinic acid with 8 to 24 carbon atoms in the alkyl group and 1 to 6 oxyethylene groups;
(g) linear alkane sulfonates containing 8 to 24 carbon atoms;
(h) linear alpha-olefin sulfonates containing 8 to 24 carbon atoms;
(i) alpha-sulfo fatty acid methyl esters of fatty acids containing 8 to 30 carbon atoms;
(j) alkyl sulfates and alkyl polyglycol ether sulfates of the Formula $R-O(CH_2-CH_2O)_x-OSO_3H$, in which R is preferably a linear alkyl group containing 8 to 30 carbon atoms and $x=0$ or 1 to 12;
(k) mixtures of surface-active hydroxysulfonates;
(l) sulfated hydroxyalkyl polyethylene glycol ethers and/or hydroxyalkylene propylene glycol ethers;
(m) sulfonates of unsaturated fatty acids with 8 to 24 carbon atoms and 1 to 6 double bonds;
(n) esters of tartaric acid and citric acid with alcohols, which represent the addition products of about 2-15 molecules of ethylene oxide and/or propylene oxide on fatty alcohols containing 8 to 22 carbon atoms;
(o) alkyl and/or alkenyl ether phosphates of Formula (E1-I),

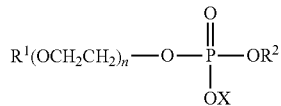

(E1-I)

wherein $R^1$ preferably stands for an aliphatic hydrocarbon group containing 8 to 30 carbon atoms, $R^2$ stands for hydrogen, a $(CH_2CH_2O)_n R^1$ group or X, h for numbers between 1 and 10 and X for hydrogen, an alkali metal or alkaline earth metal or $NR^3R^4R^5R^6$, with $R^3$ to $R^6$, independently of each other standing for a $C_1$ to $C_4$ hydrocarbon group;
(p) sulfated fatty acid alkylene glycol esters of Formula (E1-11), $R^7CO(AlkO)_nSO_3M$, wherein $R^7CO-$ stands for a linear or branched, aliphatic, saturated and/or unsaturated acyl group containing 6 to 22 carbon atoms, Alk for $CH_2CH_2$, $CHCH_3CH_2$ and/or $CH_2CHCH_3$, n for numbers from 0.5 to 5 and M for a cation, as are described in DE-OS 197 36 906;
(q) amido ether carboxylic acids; and
(r) condensation products of $C_8$-$C_{30}$ fatty alcohols with protein hydrolyzates and/or amino acids and their derivatives, which are known to the person skilled in the art as albumin fatty acid condensates, such as for example the Lamepon® types, Gluadin® types, Hostapon® KCG or the Amisofi® types.

Zwitterionic surfactants are designated as those surface-active compounds that carry at least one quaternary ammonium group and at least one $-COO^{(-)}$ or $-SO_3^{(-)}$ group in the molecule. Particularly suitable zwitterionic surfactants are the so-called betaines such as the N-alkyl-N,N-dimethylammonium glycinates, for example the cocoalkyl-dimethylammonium glycinate, N-acyl-aminopropyl-N,N-dimethylammonium glycinate, for example the coco-acylaminopropyl-dimethylammonium glycinate, and 2-alkyl-3-carboxymethyl-3-hydroxyethyl-imidazolines each with 8 to 18 carbon atoms in the alkyl or acyl group as well as the cocoacyl-aminoethylhydroxyethylcarboxymethyl glycinate. A preferred zwitterionic surfactant is the fatty acid amide derivative, known under the INCI name Cocamidopropyl Betaine.

Ampholytes are understood to include such surface-active compounds that apart from a $C_{8-24}$ alkyl or acyl group, comprise at least one free amino group and at least one $-COOH$ or $-SO_3H$ group in the molecule, and are able to form internal salts. Examples of suitable ampholytes are N-alkylglycines, N-alkyl propionic acids, N-alkylamino butyric acids, N-alkylimino dipropionic acids, N-hydroxyethyl-N-alkylamidopropylglycines, N-alkyltaurines, N-alkylsarcosines, 2-alkylamino propionic acids and alkylamino acetic acids, each with about 8 to 24 carbon atoms in the alkyl group. Particularly preferred ampholytes are N-cocoalkylamino propionate, the cocoacylaminoethylamino propionate and the $C_{12-18}$ acyl sarcosine.

The agents according to the invention comprise the ingredients or active substances in a cosmetically acceptable carrier.

Preferred cosmetically acceptable carriers are aqueous, alcoholic or aqueous alcoholic media containing preferably at least 10 wt % water, based on the total composition. In particular, lower alcohols containing 1 to 4 carbon atoms, such as for example ethanol and isopropanol, which are usually used for cosmetic purposes, can be comprised as alcohols.

Organic solvents or a mixture of solvents with a boiling point of less than 400° C. can be comprised as the additional co-solvents in a quantity of 0.1 to 15 weight percent, preferably 1 to 10 weight percent, based on the total agent. Particularly suitable additional co-solvents are propylene glycol, polyethylene glycol, polypropylene glycol, unbranched or branched hydrocarbons such as pentane, hexane, isopentane and cyclic hydrocarbons such as cyclopentane and cyclohexane.

The agents preferably exhibit a pH of 2 to 11. The pH range is particularly preferably between 2 and 8. In the context of this publication, the pH data refer to the pH at 25° C. unless otherwise stated.

The agents according to the invention can additionally comprise the auxiliaries and additives that are usually incorporated into styling agents. In particular, additional care products may be mentioned as suitable auxiliaries and additives.

Preferably, at least one silicone oil and/or at least one silicone gum is used as the care substance.

Suitable silicone oils or silicone gums according to the invention are especially dialkyl and alkylarylsiloxanes, such as, for example dimethylpolysiloxane and methylphenylpolysiloxane, as well as their alkoxylated, quaternized or also anionic derivatives. Cyclic and linear polydialkylsiloxanes, their alkoxylated and/or aminated derivatives, dihydroxypolydimethylsiloxanes and polyphenylalkylsiloxanes are preferred.

Silicone oils afford the most varied effects. Thus, for example, they simultaneously influence the dry and wet compatibility, the feel of the dry and wet hair as well as the gloss. The term, "silicone oils" is understood by the person skilled in the art to mean organosilicon compounds with a plurality of structures. In the first instance among these are understood the Dimethiconols (S1). They can be both linear as well as branched as well as cyclic or cyclic and branched.

Further suitable silicones are amino-functional silicones, especially the silicones compiled under the INCI name Amodimethicone. Consequently, it is inventively preferred when the agents according to the invention additionally comprise at least one amino-functional silicone. These are understood to be silicones that possess at least one, optionally substituted, amino group.

The agents preferably comprise the silicones in amounts of 0.01 wt % to 15 wt %, particularly preferably 0.05 to 2 wt %, based on the total agent.

The agent can comprise, for example at least one protein hydrolysate and/or one of its derivatives as a care substance of another compound class.

Protein hydrolysates are product mixtures obtained by acid-, base- or enzyme-catalyzed degradation of proteins (albumins). According to the invention, the term "protein hydrolysate" is also understood to mean total hydrolysate as well as individual amino acids and their derivatives as well as mixtures of different amino acids. Furthermore, according to the invention, polymers built up from amino acids and amino acid derivatives are understood to be included in the term protein hydrolysate. The molecular weight of the protein hydrolysate suitable according to the invention ranges between 75, the molecular weight of glycine, and 200,000, preferably the molecular weight is 75 to 50,000 and quite particularly preferably 75 to 20,000 Dalton.

According to the invention, the added protein hydrolyzates can be of vegetal as well as animal or marine or synthetic origin.

Animal protein hydrolysates are, for example, elastin, collagen, keratin, silk protein, and milk albumin protein hydrolysates, which can also be present in the form of their salts. Such products are marketed, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex), Sericin (Pentapharm) and Kerasol® (Croda).

Protein hydrolysates of vegetal origin, e.g. soya-, almond-, pea-, potato- and wheat protein hyrolyzates, are available, for example, under the trade names Gluadin® (Cognis), DiaMin® (Diamalt), Lexein® (Inolex), Hydrosoy® (Croda), Hydrolupin® (Croda), Hydrosesame® (Croda), Hydrotritium® (Croda) and Crotein® (Croda).

The agents according to the invention comprise the protein hydrolysates, for example, in concentrations of 0.01 wt % to 20 wt %, preferably 0.05 wt % up to 15 wt % and quite particularly preferably in amounts of 0.05 wt % up to 5.0 wt %, each based on the total end-use preparation.

The agent according to the invention can further comprise at least one vitamin, one provitamin, one vitamin precursor and/or one of their derivatives as the care substance.

According to the invention, such vitamins, provitamins and vitamin precursors are preferred, which are normally classified in the groups A, B, C, E, F and H.

The agents according to the invention preferably comprise vitamins, provitamins and vitamin precursors from groups A, B, C, E and H.

Panthenol, pantolactone, pyridoxine and its derivatives as well as nicotinamide and biotin are especially preferred.

D-panthenol is quite particularly preferably employed as a care substance, optionally in combination with at least one of the abovementioned silicone derivatives.

The addition of panthenol increases the flexibility of the polymer film formed when the agent according to the invention is used. Accordingly, if a particularly flexible hold is desired, then the agents according to the invention can additionally comprise panthenol. In a preferred embodiment, the agents according to the invention comprise panthenol, preferably in a quantity of 0.05 to 10 wt %, particularly preferably 0.1 to 5 wt %, each based on the total agent.

The agents according to the invention can further comprise at least one plant extract as a care substance. Usually, these extracts are manufactured by extraction of the whole plant. In individual cases, however, it can also be preferred to produce the extracts solely from blossoms and/or leaves of the plant. With regard to the inventively preferred plant extracts, reference is particularly made to extracts that are listed in the Table beginning on page 44 of the 3rd edition of the Guidelines for the Declaration of Ingredients in Cosmetics, (Leitfadens zur Inhaltsstoffdeklaration kosmetischer Mittel) published by the German Cosmetics, Toiletry, Perfumery and Detergent Association e.V. (IKW), Frankfurt. According to the invention, mainly extracts from green tea, oak bark, stinging nettle, hamamelis, hops, henna, camomile, burdock root, field horsetail, hawthorn, linden flowers, almonds, aloe vera, spruce needles, horse chestnut, sandal wood, juniper, coconut, mango, apricot, lime, wheat, kiwi, melons, orange, grapefruit, sage, rosemary, birch, malva, lady's smock, common yarrow, wild thyme, lemon balm, thyme rest-harrow, coltsfoot, marshmallow (althaea), meristem, ginseng and ginger are preferred.

Mono- or oligosaccharides can also be incorporated as the care substance into the agents according to the invention.

Both monosaccharides as well as oligosaccharides, such as for example raw sugar, lactose and raffinose, can be incorporated. According to the invention, the use of monosaccharides is preferred. Once again, the monosaccharides preferably include those compounds that contain 5 or 6 carbon atoms. Glucose is quite particularly preferably used, and is suitable both in the D(+) or L(−) configuration or as the racemate. In addition, derivatives of these pentoses and hexoses can also be incorporated according to the invention, such as the corresponding onic and uronic acids (sugar acids), sugar alcohols, and glycosides. Preferred sugar acids are the gluconic acid, the glucuronic acid, the sugar acids, the mannosugar acids and the mucic acids. Preferred sugar alcohols are sorbitol, mannitol and dulcitol. Preferred glycosides are the methyl glucosides. The inventive agents preferably comprise the mono or oligosaccharides in an amount of 0.1 to 8 wt %, particularly preferably 1 to 5 wt %, based on the total end-use preparation.

The agent can further comprise at least one lipid as a care substance. According to the invention, suitable lipids are phospholipids, for example soy lecithin, egg lecithin and cephalins as well as the substances known under the INCI names Linoleamidopropyl PG-Dimonium Chloride Phosphate, Cocamidopropyl PG-Dimonium Chloride Phosphate and Stearamidopropyl PG-Dimonium Chloride Phosphate. These are commercialized, for example, by the Mona Company under the trade names Phospholipid EFA®, Phospholipid PTC® and Phospholipid SV®. The compositions according to the invention preferably comprise the lipids in amounts of 0.01 to 10 wt %, in particular 0.1 to 5 wt %, based on the total end-use preparation.

By the addition of a UV filter, both the agent itself as well as the treated fibers can be protected against damage from UV radiation. Consequently, at least one UV filter is preferably added to the agent. The suitable UV filters are not generally limited in regard to their structure and their physical properties. Indeed, all UV filters that can be employed in the cosmetic field having an absorption maximum in the UVA (315-400 nm), in the UVB (280-315 nm) or in the UVC (<280 nm) regions are suitable. UV filters having an absorption maximum in the UVB region, especially in the range from about 280 to about 300 nm, are particularly preferred.

The inventively preferred UV-filters are chosen from substituted benzophenones, p-aminobenzoates, diphenylacrylates, cinnamates, salicylates, benzimidazoles and o-aminobenzoates.

The agent usually comprises the UV filters in quantities of 0.01 to 5 wt %, based on the total end-use preparation. Quantities of 0.1-2.5 wt % are preferred.

In a particular embodiment, the agent according to the invention further comprises one or more substantive dyes. Application of the agent then enables the treated keratinic fiber not only to be temporarily styled but also to be dyed at the same time. This can be particularly desirable when only a temporary dyeing is desired, for example with flamboyant fashion colors that can be subsequently removed from the keratinic fibers by simply washing them out.

Substantive dyes are usually nitrophenylenediamines, nitroamino phenols, azo dyes, anthraquinones or indophenols. The inventive agents according to this embodiment comprise the substantive dyes preferably in a quantity of 0.001 to 20 wt %, based on the total agent.

In the context of another embodiment, the agent according to the invention is preferably in the form of a cream or a gel, particularly as a gel.

In this regard it is again preferred when gas bubbles are incorporated into the inventive cream or into the inventive gel. These gas bubbles are visible to the human eye. Air, nitrogen, oxygen, carbon dioxide, dinitrogen monoxide, argon are exemplary suitable as the gases.

The viscosity of the agents according to the invention in the form of creams or gels is preferably from 10 000 to 500 000 mPas, particularly preferably from 30 000 to 300 000 mPas, (each measured with Brookfield RVDV II+ with Heilpath, Spindel T-E, 5 rpm, 20° C.).

If the agent according to the invention is in the form of a gel, then it is particularly preferably a transparent gel.

A second subject matter of the invention is the use of the agent according to the invention for the temporary shaping of hair and/or for hair care.

The agents according to the invention and products that comprise these agents, especially hair gels or hair creams, are particularly characterized in that they lend to the treated hair a very strong, long-lasting hold to the hairstyle, although the hair remains flexible. If the agent is presented as a hair gel, then the gel has a pasty consistency that nevertheless can be uniformly dispersed on the hair without any dripping.

It is inventively preferred to use the agent of the first subject matter of the invention as a leave-on hair treatment agent.

A third subject matter of the invention is a method for treating keratin-containing fibers, especially human hair, in which method the inventive agent of the first subject matter of the invention is applied onto the keratin-containing fibers.

It is inventively preferred when the keratin-containing fibers are styled before, during or after the application of the agent according to the invention.

Furthermore it is inventively preferred in the context of the method according to the invention, not to rinse out the agent according to the invention from the keratin-containing fibers.

The following examples are intended to illustrate the subject matter of the present invention in more detail, without limiting it in any way.

EXAMPLES 1.0 Formulations

The cosmetic agents A to I shown in the following TABLE were manufactured. Unless otherwise stated, the quantities are understood to be in weight percent. The agents A to I could be well dispersed on the hair, produced a good hair set and simultaneously an excellent hair care.

| Ingredients (weight %) | Cosmetic Agents | | | | | | | | |
| --- | --- | --- | --- | --- | --- | --- | --- | --- | --- |
| | A | B | C | D | E | F | G | H | I |
| Glycerin | 7.50 | 5.50 | 3.50 | 4.50 | 5.50 | 7.50 | 7.50 | 7.50 | 2.50 |
| Glyceryl Acrylates/Acrylic Acid Copolymer | 0.04 | 0.04 | 0.04 | 0.04 | 0.03 | 0.03 | 0.03 | 0.03 | 0.02 |
| PVM/MA copolymer[1] | 0.03 | 0.03 | 0.03 | 0.03 | 0.02 | 0.02 | 0.02 | 0.02 | 0.01 |
| Ceraphyl ODS[2] | 3.00 | 1.50 | 0.50 | 1.50 | — | 1.50 | 1.50 | 1.50 | 1.20 |
| Ceraphyl 55[3] | 3.00 | 3.00 | — | 3.00 | — | — | — | — | — |
| Ceraphyl 230[4] | — | 1.50 | 1.50 | — | 3.00 | 2.00 | — | 0.50 | — |
| Cetiol CC[5] | 4.50 | — | 3.00 | 1.50 | 1.50 | — | 2.00 | 3.50 | 1.00 |
| CETIOL LDO[6] | — | — | — | — | 2.00 | — | — | — | — |
| PVP/VA 60/40 W[7] | 11.00 | 11.00 | 11.00 | — | 3.00 | 2.00 | 5.00 | — | — |
| Luviskol K 85[8] | — | 5.00 | — | 8.00 | 7.00 | 4.00 | 17.00 | 15.0 | — |
| Luviquat Hold[9] | 2.00 | — | — | 3.00 | — | — | — | 5.00 | — |
| Simulgel SMS 88[10] | 2.80 | 3.50 | 2.00 | 1.50 | 3.00 | 2.80 | 4.00 | 2.80 | 3.00 |
| Abil Quat 3272[11] | 1.00 | — | 1.00 | 1.00 | 1.00 | — | 0.10 | 0.10 | 0.50 |
| D-Panthenol | 0.15 | 0.15 | 0.15 | 0.15 | 0.15 | 0.15 | 0.15 | 0.15 | 0.15 |
| PEG-40 Hydr. castor oil | 0.50 | 0.50 | 0.50 | 0.50 | 0.50 | 0.50 | 0.50 | 0.50 | 0.50 |
| Neolone PE[12] | 0.60 | 0.60 | 0.60 | 0.40 | 0.60 | 0.60 | 0.60 | 0.60 | 0.60 |
| Phenoxyethanol, pure | — | — | — | 0.30 | — | — | 0.30 | — | — |
| Monomuls 90 0 18[13] | — | — | — | 1.00 | 1.00 | 0.50 | 0.50 | 0.10 | — |
| Cetyltrimethylammonium chloride | — | — | — | 0.20 | 0.20 | — | — | — | — |

| Ingredients (weight %) | Cosmetic Agents | | | | | | | | |
|---|---|---|---|---|---|---|---|---|---|
| | A | B | C | D | E | F | G | H | I |
| Benzophenone-4 | — | — | — | — | — | 0.10 | 0.10 | 0.10 | — |
| Dow Corning 5330 Fluid[14] | — | 5.00 | — | 2.00 | — | 2.00 | 1.50 | 0.50 | — |
| DOW CORNING 556[15] | — | — | — | — | 2.00 | 1.50 | 1.00 | 1.00 | 5.00 |
| Perfume | 0.30 | 0.30 | 0.50 | 0.50 | 0.10 | 0.30 | 0.30 | 0.30 | 0.20 |
| Water, deionized | | | | ad 100 | | | | | |

Table Notes:
[1] copolymer of maleic anhydride and methyl vinyl ether;
[2] 2-octyldodecyl stearate (INCI name: Octyldodecyl Stearate) (ISP);
[3] tridecyl neopentanoate (INCI name: Tridecyl Neopentanoate) (ISP);
[4] adipic acid diisopropyl ester (INCI name: Diisopropyladipate) (ISP);
[5] dioctyl carbonate (INCI name: Dicaprylyl Carbonate) (Cognis);
[6] mixture of dioctyl carbonate and $C_{12}$-/$C_{14}$ fatty alcohol (ca. 40 wt % fatty alcohol fraction) (Cognis);
[7] copolymer of vinyl acetate and N-vinyl pyrrolidone in the ratio 40 to 60 (50% active substance in water, INCI name: VP/VA Copolymer) (BASF);
[8] polyvinyl pyrrolidone (ca. 20% solids in water; INCI name: PVP) (BASF);
[9] copolymer of N-vinyl pyrrolidone, N-vinyl caprolactam and quaternized, permanently cationic N-vinyl imidazole (methyl sulfate) in the weight ratio (40/50/10) (20 wt % polymer dissolved in water, molecular weight ca. 700 000 g/mol, charge density at pH 7: 0.8 meq/g; INCI name: Polyquaternioum-46) (BASF);
[10] copolymer of sodium acrylate, sodium acryloyldimethyltaurate and dimethylacrylamide (inverse, auto-inversible Latex mit Isohexadecan and Polysorbate-60, ca. 20 wt % solids in water) (Seppic);
[11] 3-(3-(3-cocoamidopropyl)dimethylammonio)-2-hydroxypropyl)propyl-terminated silicone (CAS-No.: 134737-05-6; 50 wt % active substance in water; INCI name: Quaternium-80) (Evonik Goldschmidt);
[12] 2-methyl-2H-isothiazolin-3-one (ca. 1.55% in 2-phenoxyethanol; INCI name: Phenoxyethanol, Methylisothiazolinone) (Rohm & Haas);
[13] oleic acid monoglyceride (INCI name: Glyceryl Oleate) (Cognis);
[14] water-soluble polyether polysiloxane copolymer (INCI name: PEG/PPG-15/15 Dimethicone) (Dow Corning); and
[15] polyphenylmethylsiloxane (INCI name: Phenyl Trimethicone) (Dow Corning).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

We claim:

1. A method for the temporary shaping of hair, said method comprising the step of contacting hair with an agent for treating keratin-containing fibers comprising:

a. at least one copolymer comprising at least one structural unit (I) and at least one structural unit (II):

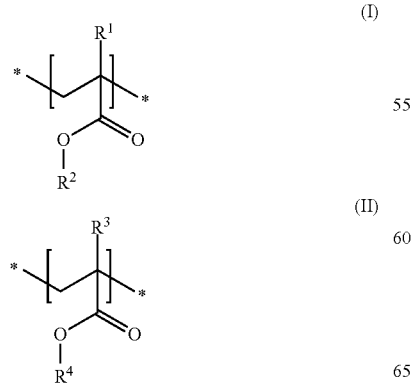

wherein $R^1$ and $R^3$ independently denote hydrogen or a methyl group; $R^2$ denotes a dihydroxypropyl group optionally substituted with a glyceryl group or an oligoglyceryl group of 2 to 10 glyceryl units; and $R^4$ denotes hydrogen or a ($C_1$ to $C_4$) alkyl group;

b. at least one of a film-forming or setting polymer; and c. at least one ester oil, wherein (a), (b), and (c) are present in a cosmetically acceptable carrier and the agent is a powdered composition.

2. The method according to claim 1, wherein said structural unit (I) comprises at least one structural unit (I-1),

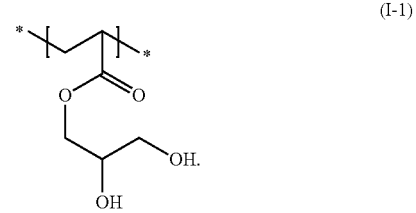

3. The method according to claim 1, wherein said copolymer comprises glycerylacrylates/acrylates.

4. The method according to claim 1, wherein said film-forming or setting polymer is chosen from the group consisting of cationic polymers, nonionic polymers, and mixtures thereof.

5. The method according to claim 1, wherein said ester oil comprises the combination of:

a. at least one ester selected from the group consisting of:
Formula (III),

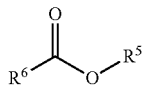 (III)

wherein $R^5$ denotes a linear or branched ($C_3$ to $C_{20}$) alkyl group and $R^6$ denotes a linear ($C_3$ to $C_{17}$) alkyl group, a branched ($C_3$ to $C_{17}$) alkyl group, or a ($C_2$ to $C_6$) hydroxyalkyl group,
Formula (IV),

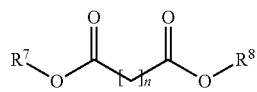 (IV)

wherein $R^7$ and $R^8$ independently denote a linear or branched ($C_3$ to $C_{10}$) alkyl group and n denotes a whole number from 2 to 6,
and mixtures thereof; and
b. at least one ester having Formula (V),

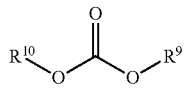 (V)

wherein $R^9$ and $R^{10}$ independently denote a linear or branched ($C_4$ to $C_{18}$) alkyl group.

6. The method according to claim 1, wherein said copolymer is present from 0.001 wt % to 1.0 wt % based on the total weight of the agent.

7. The method according to claim 6, wherein said copolymer is present from 0.005 to 0.1 wt % based on the total weight of the agent.

8. The method according to claim 1, wherein said film-forming or setting polymer is present from 0.01 to 20 wt % based on the total weight of the agent.

9. The method according to claim 8, wherein said film-forming or setting polymer is present from 2.0 to 10.0 wt % based on the total weight of the agent.

10. The method according to claim 1, wherein said ester oil is present from 0.5 to 30 wt % based on the total weight of the agent.

11. The method according to claim 10, wherein said ester oil is present from 1 to 20 wt % based on the total eight of the agent.

12. The method according to claim 1, further comprising from 1.0 to 10 wt % of a ($C_2$ to $C_6$) polyol based on the total weight of the agent.

13. The method according to claim 12, wherein said polyol is glycerin.

14. The method according to claim 1, further comprising at least one sulfonic acid polymer containing at least one structural unit (P-I) and at least one structural unit (P-II):

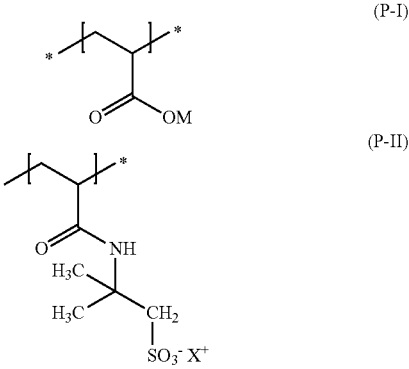

wherein M denotes hydrogen or sodium and X denotes a physiologically acceptable cation.

15. The method according to claim 14, wherein said sulfonic acid polymer is present from 0.1 to 10 wt % based on the total weight of the agent.

16. The method according to claim 15, wherein said sulfonic acid polymer is present from 1 to 5 wt % based on the total weight of the agent.

* * * * *